(12) United States Patent  
Bradbury et al.

(10) Patent No.: US 7,659,399 B2  
(45) Date of Patent: *Feb. 9, 2010

(54) 1-THIA-2,4A-DIAZA-CYCLOPENTA[B] NAPTHTHALENE-3,4-DIONES AND RELATED COMPOUNDS AS ANTI-INFECTIVE AGENTS

(75) Inventors: Barton James Bradbury, Wallingford, CT (US); Jason Allan Wiles, Hamden, CT (US)

(73) Assignee: Achillion Pharmaceuticals, Inc., New Haven, CT (US)

( * ) Notice: Subject to any disclaimer, the term of this patent is extended or adjusted under 35 U.S.C. 154(b) by 709 days.

This patent is subject to a terminal disclaimer.

(21) Appl. No.: 11/326,109

(22) Filed: Jan. 5, 2006

(65) Prior Publication Data

US 2007/0129333 A1 Jun. 7, 2007

Related U.S. Application Data

(60) Provisional application No. 60/641,548, filed on Jan. 5, 2005.

(51) Int. Cl.
C07D 417/04 (2006.01)
C07D 513/04 (2006.01)
A61K 31/4365 (2006.01)

(52) U.S. Cl. .................. 546/83; 546/115; 514/278; 514/293

(58) Field of Classification Search ............ 546/83, 546/115; 514/278, 293  
See application file for complete search history.

(56) References Cited

U.S. PATENT DOCUMENTS

| | | | |
|---|---|---|---|
| 4,767,762 A | 8/1988 | Chu | |
| 4,945,160 A | 7/1990 | Kiely et al. | |
| 5,071,848 A | 12/1991 | Chu et al. | |
| 5,387,748 A | 2/1995 | Demuth, Jr. et al. | |
| 5,519,016 A | 5/1996 | Kimura et al. | |
| 5,580,872 A | 12/1996 | Chu et al. | |
| 5,631,256 A | 5/1997 | Demuth, Jr. et al. | |
| 5,645,163 A | 7/1997 | Werth | |
| 5,688,791 A | 11/1997 | Kimura et al. | |
| 7,199,128 B2 * | 4/2007 | Bradbury et al. ............ | 514/278 |

FOREIGN PATENT DOCUMENTS

| | | |
|---|---|---|
| EP | 0 227 039 A1 | 7/1987 |
| EP | 0 394 120 A1 | 4/1990 |
| EP | 0878194 | 11/1998 |
| JP | 01-160985 | 6/1989 |
| JP | 01-193275 | 8/1989 |
| JP | 01-265092 | 10/1989 |
| JP | 02-174784 | 7/1990 |
| JP | 02-243692 | 9/1990 |
| JP | 02-255687 | 10/1990 |
| JP | 03-058992 | 3/1991 |
| JP | 03-209367 | 9/1991 |
| JP | 10-130149 | 5/1998 |
| WO | WO 95/29894 | 11/1995 |
| WO | WO 2005/019228 A1 | 3/2005 |

OTHER PUBLICATIONS

Dorwald F. A. Side Reactions in Organic Synthesis, 2005, Wiley: VCH, Weinheim p. IX of Preface.*  
Li, Qun et al., "Synthesis and Structure-Activity Relationships of 2-Pyridones: A Novel Series of Potent DNA Gyrase Inhibitors as Antibacterial Agents," *J. Med. Chem.* (1996) 39: 3070-3088.  
Wiles, Jason A. et al., "Isothiazolopyridones: Synthesis, Structure, and Biological Activity of a New Class of Antibacterial Agents," *J. Med. Chem.* (2006) 49: 39-42.  
Frigola, Jordi et al., "7-Azetidinylquinolones as Antibacterial Agents. Synthesis and Structure-Activity Relationships," *J. Med. Chem.* (1993) 36: 801-810.  
Ishiyama, Tatsuo et al., "Palladium (0)-Catalyzed Cross-Coupling Reaction of Alkoxydiboron with Haloarenes: A Direct Procedure for Arylboronic Esters," *J. Org. Chem.* (1995) 60: 7508-7510.

(Continued)

*Primary Examiner*—Rita J Desai  
(74) *Attorney, Agent, or Firm*—Cantor Colburn LLP

(57) ABSTRACT

The invention provides compounds and salts of Formula I and Formula II:

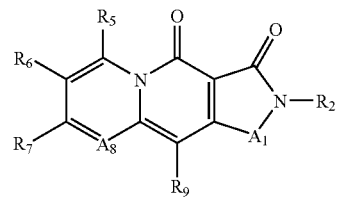

Formula I

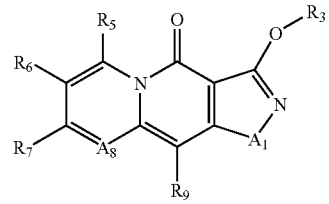

Formula II which possess antimicrobial activity. The invention also provides novel synthetic intermediates useful in making compounds of Formula I and Formula II. The variables $A_1$, $A_8$, $R_2$, $R_3$, $R_5$, $R_6$, $R_7$, and $R_9$ are defined herein.

Certain compounds of Formula I and Formula II disclosed herein are potent and selective inhibitors of bacterial DNA synthesis and bacterial replication. The invention also provides antimicrobial compositions, including pharmaceutical compositions, containing one or more compounds of Formula I or Formula II and one or more carriers, excipients, or diluents. Such compositions may contain a compound of Formula I or Formula II as the only active agent or may contain a combination of a compound of Formula I or Formula II and one or more other active agents. The invention also provides methods for treating microbial infections in animals.

19 Claims, No Drawings

OTHER PUBLICATIONS

Kiely, John S. et al., "Synthesis of 7-(Alkenyl, Cycloalkenyl, and 1,2,3,6-Tetrahydro-4-pyridinyl)quinolones," *J. Heterocyclic Chem.*, (1991) 28: 1581-1585.

Laborde, Edgardo et al., Novel 7-Substituted Quinolone Antibacterial Agents. Synthesis of 7-Alkenyl, Cycloalkenyl, and 1,2,3,6-Tetrahydro-4-pyridinyl-1,8-naphthyridines [1], *J.Heterocyclic Chem.*, (1991) 28: 191-198.

Laborde, Edgardo et al., "Quinolone Antibacterials: Synthesis and Biological Activity of Carbon Isosteres of the 1-Piperazinyl and 3-Amino-1-pyrrolidinyl Side Chains[1]," *J. Med. Chem.* (1992) 36: 1964-1970.

Li, Qun et al., "Synthesis and Structure-Activity Relationships of 2-Pyridones: A Novel Series of Potent DNA Gyrase Inhibitors as Antibacterial Agents," *J. Med. Chem.* (1996) 39: 3070-3088.

Otten, Pieter A. et al., "4-Oxo-4H-quinolizine-3-carboxylic Acids as $Mg^{2+}$ Selective, Fluorescent Indicators," *Bioconjugate Chem.* (2001) 12: 203-212.

Tamao, Kohei and Miyaura, Norio, "Introduction to Cross-Coupling Reactions," *Topics in Current Chemistry* (2002) 219:1-9.

Wiles, J. A. et al., "General, Efficient, One-Step Synthesis," *J. Med.. Chem.*, (2006) 49: 39-42.

\* cited by examiner

1-THIA-2,4A-DIAZA-CYCLOPENTA[B] NAPHTHALENE-3,4-DIONES AND RELATED COMPOUNDS AS ANTI-INFECTIVE AGENTS

CROSS REFERENCE TO RELATED APPLICATION

This application claims priority from U.S. Provisional application 60/641,548 filed Jan. 5, 2005, which is hereby incorporated by reference in its entirety.

FIELD OF THE INVENTION

The present invention provides 1-thia-2,4a-diaza-cyclopenta[b]naphthalene-3,4-diones and related compounds, which possess antimicrobial activity. Certain compounds provided herein possess potent antibacterial, antiprotozoal, or antifungal activity. Particular compounds provided herein are also potent and/or selective inhibitors of prokaryotic DNA synthesis and prokaryotic reproduction. The invention provides anti-microbial compositions, including pharmaceutical compositions, containing one or more carrier, diluents, or excipients. The invention provides pharmaceutical compositions containing a 1-thia-2,4a-diaza-cyclopenta[b]naphthalene-3,4-dione or related compound as the only active agent or containing a 1-thia-2,4a-diaza-cyclopenta[b]naphthalene-3,4-dione or related compound in combination with one or more other active agent, such as one or more other antimicrobial or antifungal agent. The invention provides methods for treating or preventing microbial infections in eukaryotes, preferably animals, by administering an effective amount of a 1-thia-2,4a-diaza-cyclopenta[b]naphthalene-3,4-dione or related compound to a eukaryote suffering from or susceptible to microbial infection. The invention also provides methods of inhibiting microbial growth and survival by applying an effective amount of a 1-thia-2,4a-diaza-cyclopenta[b]naphthalene-3,4-dione or related compound.

The invention also provides novel intermediates useful for the for the synthesis of 1-thia-2,4a-diaza-cyclopenta[b]naphthalene-3,4-diones and related compounds. The invention also provides methods of synthesis of 1-thia-2,4a-diaza-cyclopenta[b]naphthalene-3,4-diones and related compounds.

BACKGROUND OF THE INVENTION

Antimicrobial compounds are compounds capable of destroying or suppressing the growth or reproduction of microorganisms, such as bacteria, protozoa, mycoplasma, yeast, and fungi. The mechanisms by which antimicrobial compounds act vary. However, they are generally believed to function in one or more of the following ways: by inhibiting cell wall synthesis or repair; by altering cell wall permeability; by inhibiting protein synthesis; or by inhibiting synthesis of nucleic acids. For example, beta-lactam antibacterials inhibit the essential penicillin binding proteins (PBPs) in bacteria, which are responsible for cell wall synthesis. Quinolones act, at least in part, by inhibiting synthesis of DNA, thus preventing the cell from replicating.

Many attempts to produce improved antimicrobials yield equivocal results. Indeed, few antimicrobials are produced that are truly clinically acceptable in terms of their spectrum of antimicrobial activity, avoidance of microbial resistance, and pharmacology. Thus there is a continuing need for broad-spectrum antimicrobials, and a particular need for antimicrobials effective against resistant microbes.

Pathogenic bacteria are known to acquire resistance via several distinct mechanisms including inactivation of the antibiotic by bacterial enzymes (e.g., beta-lactamases that hydrolyze penicillin and cephalosporins); removal of the antibiotic using efflux pumps; modification of the target of the antibiotic via mutation and genetic recombination (e.g., penicillin-resistance in *Neiserria gonorrhea*); and acquisition of a readily transferable gene from an external source to create a resistant target (e.g., methicillin-resistance in *Staphylococcus aureus*). There are certain gram-positive pathogens, such as vancomycin-resistant *Enterococcus faecium*, which are resistant to virtually all commercially available antibiotics.

Resistant organisms of particular note include methicillin-resistant and vancomycin-resistant *Staphylococcus aureus*, penicillin-resistant *Streptococcus pneumoniae*, vancomycin-resistant enterococci, fluoroquinolone-resistant *E. coli*, cephalosporin-resistant aerobic gram-negative rods and imipenem-resistant *Pseudomonas aeruginosa*. These organisms are significant causes of nosocomial infections and are clearly associated with increasing morbidity and mortality. The increasing numbers of elderly and immunocompromised patients are particularly at risk for infection with these pathogens. Therefore, there is a large unmet medical need for the development of new antimicrobial agents.

SUMMARY OF THE INVENTION

The invention provides compounds of Formula I and Formula II (shown below) and includes 1-thia-2,4a-diaza-cyclopenta[b]naphthalene-3,4-dione and related compounds, which possess antimicrobial activity. The invention provides compounds of Formula I and Formula II that possess potent and/or selective antibacterial, antiprotozoal, or antifungal activity. The invention also provides anti-bacterial compositions containing one or more compounds of Formula I or Formula II, or a salt, solvate, or acylated prodrug of such a compound, and one or more carriers, excipients, or diluents.

The invention further comprises methods of treating and preventing microbial infections, particularly bacterial and protozoal infections by administering and effective amount of a compound of Formula I or Formula II to a eukaryote suffering from or susceptible to a microbial infection. These microbial infections include bacterial infections, for example *E. coli* infections, *Staphylococcus* infections, *Salmonella* infections and protozoal infections, for example *Chlamydia* infections. The invention is particularly includes methods of preventing or treating microbial infections in mammals, including humans, but also encompasses methods of preventing or treating microbial infections in other animals, including fish, birds, reptiles, and amphibians.

Methods of treatment include administering a compound of Formula I or Formula II alone as the single active agent or administering a compound of Formula I in combination with one or more other therapeutic agent, such as an antibacterial, an antifungal, an antiviral, an interferon, an efflux-pump inhibitor, a beta-lactamase inhibitor, or another compound of Formula I or Formula II.

The invention also provides methods of inhibiting microbial growth and survival by applying an effective amount of an 1-thia-2,4a-diaza-cyclopenta[b]naphthalene-3,4-dione or related compound. The invention includes, for example, methods of inhibiting microbial growth and survival on medical instruments or on surfaces used for food preparation by applying a composition containing a compound of Formula I or Formula II.

Thus, the invention include compounds of Formula I and Formula II

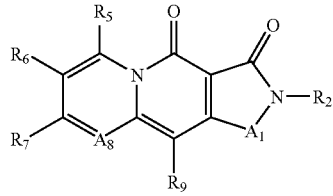

Formula I

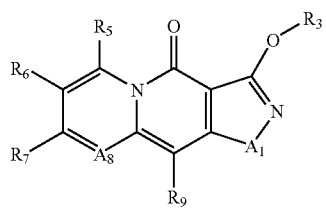

Formula II and the pharmaceutically acceptable salts thereof, wherein:

$A_1$ is S, O, SO, or $SO_2$.

$R_2$ is hydrogen, or $R_2$ is $C_1$-$C_8$alkyl, $C_2$-$C_6$alkenyl, $C_2$-$C_6$alkynyl, ($C_3$-$C_7$cycloalkyl)$C_0$-$C_4$carbohydryl, ($C_4$-$C_7$cycloalkenyl)$C_0$-$C_4$carbohydryl, (aryl)$C_0$-$C_4$carbohydryl, or ($C_2$-$C_6$heterocycloalkyl)$C_0$-$C_4$carbohydryl, each of which is substituted with 0 to 5 substituents independently chosen from halogen, hydroxy, amino, cyano, nitro, $C_1$-$C_4$alkyl, $C_1$-$C_4$alkoxy, $C_1$-$C_2$haloalkyl, $C_1$-$C_2$haloalkoxy, mono- and di-$C_1$-$C_4$alkylamino, $C_2$-$C_4$alkanoyl, $C_1$-$C_4$alkylthio, =$NOR_{10}$, =$NR_{10}$, —O(C=O)$R_{10}$, —(C=O)$NR_{10}R_{11}$, —O(C=O)$NR_{10}R_{11}$, —(C=O)$OR_{10}$, —(C=O)$NR_{10}R_{11}$, —$NR_{10}$(C=O)$R_{11}$, —$NR_{10}$(C=O)$OR_{11}$, —$NR_{10}$(C=O)$OR_{11}R_{12}$, —$NR_{10}$(C=S)$NR_{11}R_{12}$, —$NR_{10}NR_{11}R_{12}$, —$SO_3R_{10}$, —(S=O)$OR_{10}$, —$SO_2R_{13}$, —$SO_2NR_{10}R_{11}$, and —$NR_{10}SO_2R_{13}$; where $R_{10}$, $R_{11}$, and $R_{12}$ are independently hydrogen, $C_1$-$C_4$alkyl, or aryl, and $R_{13}$ is $C_1$-$C_4$alkyl or aryl.

$R_3$ is hydrogen, $C_1$-$C_6$alkyl, $C_1$-$C_6$alkanoyl, mono- or di-$C_1$-$C_6$alkylcarbamate, or $C_1$-$C_6$alkylsulfonate; each of which is substituted with 0 to 3 substituents independently chosen from halogen, hydroxy, amino, cyano, nitro, $C_1$-$C_4$alkoxy, mono- and di-$C_1$-$C_4$alkylamino, $C_1$-$C_2$haloalkyl, and $C_1$-$C_2$haloalkoxy.

$R_5$ is hydrogen, halogen, hydroxy, amino, cyano, nitro, or —$NHNH_2$, or $R_5$ is $C_1$-$C_4$alkyl, $C_1$-$C_4$alkoxy, mono- or di-($C_1$-$C_4$)alkylamino, mono-, di- or tri-$C_1$-$C_4$alkylhydrazinyl, $C_2$-$C_4$alkanoyl, $C_1$-$C_4$alkylester, $C_1$-$C_2$haloalkyl, or $C_1$-$C_2$haloalkoxy; each of which is substituted with 0 to 3 substituents independently chosen from hydroxy, amino, halogen, oxo, $C_1$-$C_4$alkoxy, $C_1$-$C_2$haloalkyl, $C_1$-$C_2$haloalkoxy, and mono- and di-$C_1$-$C_4$alkylamino.

$R_6$ is hydrogen, halogen, hydroxy, amino, cyano, $C_1$-$C_4$alkyl, $C_1$-$C_4$alkoxy, mono- or di-($C_1$-$C_4$)alkylamino, —$SO_3R_{10}$, —$SO_2R_{10}$, or —$SO_2NR_{10}R_{11}$.

$R_7$ is chloro, bromo, iodo, —O($SO_2$)$CF_3$, or —$N_2BF_4$, or $R_7$ is $XR_4$ where X is absent, —$CH_2$—$CH_2$—, —CH=CH—, —(C=O)—, —(C=O)NH—, or —C≡C—, and $R_4$ is $C_1$-$C_6$alkyl, $C_3$-$C_7$cycloalkyl, $C_3$-$C_7$cycloalkenyl, phenyl, a bicyclic 7- to 10-membered saturated, partially unsaturated, or aromatic carbocyclic group, a monocyclic or bicyclic a 5- to 10-membered bicyclic saturated, partially unsaturated, or aromatic heterocylic group bound via a carbon atom; each of which $R_4$ is substituted with 0 to 5 substituents independently chosen from (i), (ii), and (iii); where (i) is chosen from halogen, hydroxy, amino, cyano, and nitro, (ii) is chosen from $C_1$-$C_6$alkyl, $C_2$-$C_6$alkenyl, $C_2$-$C_6$alkynyl, ($C_1$-$C_6$alkoxy)$C_0$-$C_4$alkyl, mono- and di-($C_1$-$C_4$)alkylamino, $C_1$-$C_2$haloalkyl, $C_1$-$C_2$haloalkoxy, ($C_3$-$C_7$cycloalkyl)$C_0$-$C_4$carbohydryl, ($C_3$-$C_7$cycloalkyl)$C_0$-$C_4$carbohydryl-O—, ($C_4$-$C_7$cycloalkenyl)$C_0$-$C_4$carbohydryl, (aryl)$C_0$-$C_6$carbohydryl, (aryl)$C_1$-$C_4$alkoxy, ($C_2$-$C_6$heterocycloalkyl)$C_0$-$C_4$carbohydryl, (heteroaryl)$C_0$-$C_6$carbohydryl, $C_1$-$C_6$alkylthio, =$NOR_{10}$, =$NR_{10}$, —($C_0$-$C_4$alkyl)(C=O)$R_{10}$, —($C_0$-$C_4$alkyl)O(C=O)$R_{10}$, —($C_0$-$C_4$alkyl)(C=O)$NR_{10}R_{11}$, —($C_0$-$C_4$alkyl)O(C=O)$NR_{10}R_{11}$, —($C_0$-$C_4$alkyl)(C=O)$OR_{10}$, —($C_0$-$C_4$alkyl)$NR_{10}$(C=O)$R_{11}$, —($C_0$-$C_4$alkyl)$NR_{10}$(C=O)$OR_{11}$, —($C_0$-$C_4$alkyl)$NR_{10}$(C=O)$NR_{11}R_{12}$, —($C_0$-$C_4$alkyl)$NR_{10}$(C=O) ($C_1$-$C_4$alkyl)$NR_{11}$(C=O)O—$R_{12}$, —($C_0$-$C_4$alkyl)$NR_{10}$(C=S)$NR_{11}R_{12}$, —($C_0$-$C_4$alkyl)$NR_{10}NR_{11}R_{12}$, —($C_0$-$C_4$alkyl)N=$NR_{13}$, —($C_0$-$C_4$alkyl)$SO_3R_{10}$, —($C_0$-$C_4$alkyl) (S=O)$OR_{10}$, —($C_0$-$C_4$alkyl)$SO_2R_{13}$, —($C_0$-$C_4$alkyl) $SO_2NR_{10}OR_{11}$, and —($C_0$-$C_4$alkyl)$NR_{10}SO_2R_{13}$; and (iii) is chosen from —$OR_D$, —(C=O)$R_D$, —$SO_2R_D$, —$SO_3R_D$, —$NR_{10}SO_2R_D$, where $R_D$ is $C_1$-$C_4$alkyl, ($C_3$-$C_7$cycloalkyl)$C_0$-$C_2$alkyl, ($C_2$-$C_6$heterocycloalkyl)$C_0$-$C_2$alkyl, (aryl)$C_0$-$C_2$alkyl, and (heteroaryl)$C_0$-$C_2$alkyl;

where each of (ii) and (iii) is substituted with 0 to 3 substituents independently chosen from halogen, hydroxy, amino, cyano, nitro, oxo, —COOH, —$CONH_2$, $C_1$-$C_4$alkyl, $C_2$-$C_4$alkenyl, $C_2$-$C_4$alkynyl, $C_1$-$C_4$alkoxy, $C_1$-$C_4$alkoxycarbonyl, ($C_3$-$C_7$cycloalkyl)$C_0$-$C_4$carbohydryl, ($C_3$-$C_7$cycloalkyl)$C_0$-$C_4$alkoxy, mono- and di-($C_1$-$C_4$)alkylamino, $C_1$-$C_2$haloalkyl, $C_1$-$C_2$haloalkoxy, $C_2$-$C_4$alkanoyl and phenyl.

$A_8$ is N or $CR_8$ and $R_8$ is hydrogen, halogen, hydroxy, amino, cyano, nitro, or —$NHNH_2$, or $R_8$ is $C_1$-$C_4$alkyl, $C_1$-$C_4$alkoxy, mono- or di-($C_1$-$C_4$)alkylamino, mono-, di-, or tri-$C_1$-$C_4$ alkylhydrazinyl, $C_2$-$C_4$alkanoyl, $C_1$-$C_4$alkylester, $C_1$-$C_2$haloalkyl, or $C_1$-$C_2$haloalkoxy; each of which is substituted with 0 to 3 substituents independently chosen from hydroxy, amino, halogen, oxo, $C_1$-$C_4$alkoxy, $C_1$-$C_2$haloalkyl, $C_1$-$C_2$haloalkoxy, and mono- and di-$C_1$-$C_4$alkylamino.

$R_9$ is $C_1$-$C_8$alkyl, $C_1$-$C_4$alkoxy, mono- or di-($C_1$-$C_4$)alkylamino, $C_2$-$C_4$alkanoyl, $C_1$-$C_2$haloalkyl, $C_1$-$C_2$haloalkoxy, ($C_3$-$C_7$cycloalkyl)$C_0$-$C_4$alkyl, or phenyl, each of which is substituted with 0 to 3 substituents independently chosen from halogen, hydroxy, amino, cyano, nitro, —COOH, —$CONH_2$, $C_1$-$C_4$alkyl, $C_2$-$C_4$alkenyl, $C_2$-$C_4$alkynyl, $C_1$-$C_4$alkoxy, ($C_3$-$C_7$cycloalkyl)$C_0$-$C_4$alkyl, ($C_3$-$C_7$cycloalkyl)$C_0$-$C_4$alkoxy, mono- and di-($C_1$-$C_4$)alkylamino, $C_1$-$C_2$haloalkyl, $C_1$-$C_2$haloalkoxy, and $C_2$-$C_4$alkanoyl.

The invention includes novel intermediates useful for the synthesis of antimicrobial compounds of Formula I and Formula II. These intermediates are compounds of Formula I and Formula II in which $R_7$ is chloro, bromo, iodo, —O($SO_2$)$CF_3$, or —$N_2BF_4$. The invention provides methods of synthesizing compounds of Formula I and Formula II comprising coupling an intermediate of the invention to an appropriate aryl or heteroaryl boronic acid, aryl or heteroaryl boronic acid ester, or compounds substituted with Li, Mg, B, Al, Si, Zn, Cu, Zr, or Sn at the point of coupling.

DETAILED DESCRIPTION OF THE INVENTION

Chemical Description and Terminology

Prior to setting forth the invention in detail, it may be helpful to provide definitions of certain terms to be used herein. Compounds of the present invention are generally described using standard nomenclature.

In certain situations, the compounds of Formula I and Formula II may contain one or more asymmetric elements such as stereogenic centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with carbon-carbon double bonds may occur in Z- and E-forms, with all isomeric forms of the compounds being included in the present invention. In these situations, the single enantiomers, i.e., optically active forms can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column.

Where a compound exists in various tautomeric forms, the invention is not limited to any one of the specific tautomers, but rather includes all tautomeric forms.

The present invention is intended to include all isotopes of atoms occurring in the present compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

Certain compounds are described herein using a general formula that includes variables, e.g. $A_1$, $R_2$, $R_3$, $R_5$, $R_6$, $R_7$, $A_8$, and $A_9$. Unless otherwise specified, each variable within such a formula is defined independently of other variables. Thus, if a group is said to be substituted, e.g. with 0-2 R*, then said group may be substituted with up to two R* groups and R* at each occurrence is selected independently from the definition of R*. Also, combinations of substituents and/or variables are permissible only if such combinations result in stable compounds.

The term "substituted", as used herein, means that any one or more hydrogens on the designated atom or group is replaced with a selection from the indicated group, provided that the designated atom's normal valence is not exceeded. When a substituent is oxo (i.e., =O), imine (e.g. =NR), or oxime (e.g. =NOR) then 2 hydrogens on the atom are replaced. An "oxo," imine, or oxime substituent on an aromatic group or heteroaromatic group destroys the aromatic character of that group, e.g. a pyridyl substituted with oxo is pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent. Unless otherwise specified substituents are named into the core structure. For example, it is to be understood that when (cycloalkyl)alkyl is listed as a possible substituent the point of attachment of this substituent to the core structure is in the alkyl portion.

A dash ("—") that is not between two letters or symbols is used to indicate a point of attachment for a substituent. For example, —$CONH_2$ is attached through the carbon atom.

As used herein, "alkyl" is intended to include both branched and straight-chain saturated aliphatic hydrocarbon groups, having the specified number of carbon atoms. Thus, the term $C_1$-$C_6$ alkyl as used herein includes alkyl groups having from 1 to about 6 carbon atoms. When $C_0$-$C_n$ alkyl is used herein in conjunction with another group, for example, (aryl)$C_0$-$C_4$alkyl, the indicated group, in this case aryl, is either directly bound by a single covalent bond ($C_0$), or attached by an alkyl chain having the specified number of carbon atoms, in this case from 1 to about 4 carbon atoms. Examples of alkyl include, but are not limited to, methyl, ethyl, n-propyl, isopropyl, n-butyl, t-butyl, n-pentyl, and sec-pentyl. Preferred alkyl groups are lower alkyl groups, those alkyl groups having from 1 to about 8 carbon atoms or 1 to about 6 carbon atoms, e.g. $C_1$-$C_8$ and $C_1$-$C_6$alkyl groups.

"Alkenyl" as used herein, indicates a hydrocarbon chain of either a straight or branched configuration having one or more carbon-carbon double bond bonds, which may occur at any stable point along the chain. Examples of alkenyl groups include ethenyl and propenyl.

"Alkynyl" as used herein, indicates a hydrocarbon chain of either a straight or branched configuration having one or more triple carbon-carbon bonds that may occur in any stable point along the chain, such as ethynyl and propynyl.

"Carbohydryl" as used herein, includes both branched and straight-chain hydrocarbon groups, which are saturated or unsaturated, having the specified number of carbon atoms. When $C_0$-$C_n$carbohydryl is used herein in conjunction with another group, for example, (aryl)$C_0$-$C_4$carbohydryl, the indicated group, in this case aryl, is either directly bound by a single covalent bond ($C_0$), or attached by an carbohydryl chain, such as an alkyl chain, having the specified number of carbon atoms, in this case from 1 to about 4 carbon atoms. Examples include $C_1$-$C_6$alkyl, such as methyl, or 5-butyl, $C_2$-$C_6$alkynyl such and hexynyl, and $C_2$-$C_6$ alkenyl, such as 1-propenyl.

"Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. In the group "(alkoxy)alkyl" the alkoxy and alkyl groups carry the definitions set forth above and the point of attachment to the core molecule is in the alkyl.

"Alkanoyl" indicates an alkyl group as defined above, attached through a keto (—(C=O)—) bridge. Alkanoyl groups have the indicated number of carbon atoms, with the carbon of the keto group being included in the numbered carbon atoms. For example a $C_2$alkanoyl group is an acetyl group having the formula $CH_3(C=O)$—.

As used herein, the terms "mono- or di-alkylamino" or "mono- and di-alkylamino" indicate secondary or tertiary alkyl amino groups, wherein the alkyl groups are as defined above and have the indicated number of carbon atoms. The point of attachment of the alkylamino group is on the nitrogen. Examples of mono- and di-alkylamino groups include ethylamino, dimethylamino, and methyl-propyl-amino.

The term "mono- or di-alkylcarbamate" indicates 1 or 2 independently chosen alkyl groups, as defined above, attached through a carbamate (—O(C=O)NRR) linkage where each R represents an independently chosen alkyl group. Mono-alkylcarbamate groups have the formula (—O(C=O)NHR.

The term "alkylester" indicates and alkyl group as define above attached through an ester linkage in either orientation, i.e. a group of the formula —O(C=O)alkyl or a group of the formula —(C=O)Oalkyl.

The term "mono-, di-, or tri-alkylhydrazinyl" indicates from 1 to 3 independently chosen alkyl group as defined above attached through a single-bonded nitrogen-nitrogen linkage. At least one of the alkyl groups is attached to the terminal nitrogen (the nitrogen not bound to the core structure). When the term mono-alkylhydrazinyl is used only the terminal nitrogen is alkyl substituted. Examples of alkylhydrazinyl groups include 2-butyl-1-hydrazinyl, 2-butyl-2-methyl-1-hydraazinyl, and 1,2-dimethyl-2-propyl-1-hydrazinyl.

The term "alkylthio" indicates an alkyl group as defined above attached through a sulfur linkage, i.e. a group of the formula alkyl-S—. Examples include ethylthio and pentylthio.

As used herein, the term "aryl" indicates aromatic groups containing only carbon in the aromatic ring or rings. Typical aryl groups contain 1 to 3 separate, fused, or pendant rings and from 6 to about 18 ring atoms, without heteroatoms as ring members. When indicated, such aryl groups may be further substituted with carbon or non-carbon atoms or groups. Such substitution may include fusion to a 5 to 7-membered saturated cyclic group that optionally contains 1 or 2 heteroatoms independently chosen from N, O, and S, to form, for example, a 3,4-methylenedioxy-phenyl group. Aryl groups include, for example, phenyl, naphthyl, including 1-naphthyl and 2-naphthyl, and bi-phenyl.

In the term "(aryl)alkyl", aryl and alkyl are as defined above, and the point of attachment is on the alkyl group. This term encompasses, but is not limited to, benzyl, phenylethyl, and piperonyl. Likewise, in the term "(aryl)carbohydryl", aryl and carbohydryl are as defined above and the point of attachment is on the carbohydryl group, for example a phenylpropen-1-yl group.

The term "carbocyclic group" indicates a 5-6 membered saturated, partially unsaturated, or aromatic ring containing only carbon ring atoms or a 7-10 membered bicyclic saturated, partially unsaturated, or aromatic ring system containing only carbon ring atoms. Unless otherwise indicated, the carbocyclic ring may be attached to its pendant group at any carbon atom that results in a stable structure. I "Cycloalkyl" as used herein, indicates a saturated hydrocarbon ring, having the specified number of carbon atoms, usually from 3 to about 8 ring carbon atoms, or from 3 to about 7 carbon atoms. Examples of cycloalkyl groups include cyclopropyl, cyclobutyl, cyclopentyl, or cyclohexyl as well as bridged or caged saturated ring groups such as norborane or adamantane.

"Cycloalkenyl" as used herein, indicates an unsaturated, but not aromatic, hydrocarbon ring having at least one carbon-carbon double bond. Cycloalkenyl groups contain from 4 to about 8 carbon atoms, usually from 4 to about 7 carbon atoms. Examples include cyclohexenyl and cyclobutenyl.

In the terms "(cycloalkyl)alkyl," "(cycloalkyl)carbohydryl," and "(cycloalkyl)alkoxy" the terms cycloalkyl, alkyl, carbohydryl, and alkoxy are as defined above, and the point of attachment is on the alkyl, carbohydryl, or alkoxy group respectively. These terms include examples such as cyclopropylmethyl, cyclohexylmethyl, cyclohexylpropenyl, and cyclopentylethyoxy. The term (cycloalkyl)carbohydryl-O— indicates a (cycloalkyl)carbohydryl group as defined above attached via an oxygen bridge.

In the terms "(cycloalkenyl)alkyl" and "(cycloalkenyl)carbohydryl" the terms cycloalkenyl, alkyl, and carbohydryl are as defined above, and the point of attachment is on the alkyl or carbohydryl group respectively. These terms include examples such as cyclobutenylmethyl, cyclohexenylmethyl, and cyclohexylpropenyl.

"Haloalkyl" indicates both branched and straight-chain saturated aliphatic hydrocarbon groups having the specified number of carbon atoms, substituted with 1 or more halogen atoms, generally up to the maximum allowable number of halogen atoms. Examples of haloalkyl include, but are not limited to, trifluoromethyl, difluoromethyl, 2-fluoroethyl, and penta-fluoroethyl.

"Haloalkoxy" indicates a haloalkyl group as defined above attached through an oxygen bridge.

"Halo" or "halogen" as used herein refers to fluoro, chloro, bromo, or iodo.

As used herein, "heteroaryl" indicates a stable 5- to 7-membered monocyclic or 7- to 10-membered bicyclic heterocyclic ring which contains at least 1 aromatic ring that contains from 1 to 4, or preferably from 1 to 3, heteroatoms chosen from N, O, and S, with remaining ring atoms being carbon. When the total number of S and O atoms in the heteroaryl group exceeds 1, these heteroatoms are not adjacent to one another. It is preferred that the total number of S and O atoms in the heteroaryl group is not more than 2. It is particularly preferred that the total number of S and O atoms in the aromatic heterocycle is not more than 1. A nitrogen atom in a heteroaryl group may optionally be quaternized. When indicated, such heteroaryl groups may be further substituted with carbon or non-carbon atoms or groups. Such substitution may include fusion to a 5 to 7-membered saturated cyclic group that optionally contains 1 or 2 heteroatoms independently chosen from N, O, and S, to form, for example, a [1,3]dioxolo[4,5-c]pyridyl group. Examples of heteroaryl groups include, but are not limited to, pyridyl, indolyl, pyrimidinyl, pyridizinyl, pyrazinyl, imidazolyl, oxazolyl, furanyl, thiophenyl, thiazolyl, triazolyl, tetrazolyl, isoxazolyl, quinolinyl, pyrrolyl, pyrazolyl, benz[b]thiophenyl, isoquinolinyl, quinazolinyl, quinoxalinyl, thienyl, isoindolyl, and 5,6,7,8-tetrahydroisoquinoline.

In the terms "heteroarylalkyl" and "(heteroaryl)carbohydryl," heteroaryl, alkyl, and carbohydryl are as defined above, and the point of attachment is on the alkyl or carbohydryl group respectively. These terms include such examples as pyridylmethyl, thiophenylmethyl, and (pyrrolyl)1-ethyl.

The term "heterocycloalkyl" indicates a saturated cyclic group containing from 1 to about 3 heteroatoms chosen from N, O, and S, with remaining ring atoms being carbon. Heterocycloalkyl groups have from 3 to about 8 ring atoms, and more typically have from 5 to 7 ring atoms. Examples of heterocycloalkyl groups include morpholinyl, piperazinyl, piperidinyl, and pyrrolidinyl groups. A nitrogen in a heterocycloalkyl group may optionally be quaternized.

The term "heterocyclic group" indicates a 5-6 membered saturated, partially unsaturated, or aromatic ring containing from 1 to about 4 heteroatoms chosen from N, O, and S, with remaining ring atoms being carbon or a 7-10 membered bicyclic saturated, partially unsaturated, or aromatic heterocyclic ring system containing at least 1 heteroatom in the two ring system chosen from N, O, and S and containing up to about 4 heteroatoms independently chosen from N, O, and S in each ring of the two ring system. Unless otherwise indicated, the heterocyclic ring may be attached to its pendant group at any heteroatom or carbon atom that results in a stable structure.

When indicated the heterocyclic rings described herein may be substituted on carbon or on a nitrogen atom if the resulting compound is stable. A nitrogen atom in the heterocycle may optionally be quaternized. It is preferred that the total number of heteroatoms in a heterocyclic groups is not more than 4 and that the total number of S and O atoms in a heterocyclic group is not more than 2, more preferably not more than 1. Examples of heterocyclic groups include, pyridyl, indolyl, pyrimidinyl, pyridizinyl, pyrazinyl, imidazolyl, oxazolyl, furanyl, thiophenyl, thiazolyl, triazolyl, tetrazolyl, isoxazolyl, quinolinyl, pyrrolyl, pyrazolyl, benz[b]thiophenyl, isoquinolinyl, quinazolinyl, quinoxalinyl, thienyl, isoindolyl, dihydroisoindolyl, 5,6,7,8-tetrahydroisoquinoline, pyridinyl, pyrimidinyl, furanyl, thienyl, pyrrolyl, pyrazolyl, pyrrolidinyl, morpholinyl, piperazinyl, piperidinyl, and pyrrolidinyl.

Additional examples heterocyclic groups include, but are not limited to, phthalazinyl, oxazolyl, indolizinyl, indazolyl, benzothiazolyl, benzimidazolyl, benzofuranyl, benzoisoxolyl, dihydro-benzodioxinyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanonyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, 5 pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromanyl, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N oxide, indazolyl N-oxide, benzothiazolyl N-oxide, benzimidazolyl N-oxide, pyrrolyl N-oxide, oxadiazolyl N-oxide, thiadiazolyl N-oxide, tetrazolyl N-oxide, benzothiopyranyl S-oxide, and benzothiopyranyl S,S-dioxide.

As used herein "Active agents" are compounds that have pharmaceutical utility, e.g. may be used to treat a patient suffering from a disease or condition, or may be used prophylacticly to prevent the onset of a disease or condition in a patient, or that may be used to enhance the pharmaceutical activity of other compounds.

"Salts" of the compounds of the present invention include inorganic and organic acid and base addition salts. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Salts of the present compounds further include solvates of the compounds and of the compound salts.

"Pharmaceutically acceptable salts" includes derivatives of the disclosed compounds wherein the parent compound is modified by making non-toxic acid or base salts thereof, and further refers to pharmaceutically acceptable solvates of such compounds and such salts. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)$n-COOH where n is 0-4, and the like. Lists of additional suitable salts may be found, e.g., in Remington's Pharmaceutical Sciences, 17th ed., Mack Publishing Company, Easton, Pa., p. 1418 (1985).

The term "prodrugs" includes any compounds that become compounds of Formula I when administered to a mammalian subject, e.g., upon metabolic processing of the prodrug. Examples of prodrugs include, but are not limited to, acetate, formate and benzoate and like derivatives of functional groups (such as alcohol or amine groups) in the compounds of Formula I and Formula II.

The term "therapeutically effective amount" of a compound of this invention means an amount effective, when administered to a human or non-human patient, to provide a therapeutic benefit such as an amelioration of symptoms, e.g., an amount effective to decrease the symptoms of a microbial infection, and preferably an amount sufficient to reduce the symptoms of a bacterial, fungal, or protozoal infection. In certain circumstances a patient having a microbial infection may not present symptoms of being infected. Thus a therapeutically effective amount of a compound is also an amount sufficient to prevent a significant increase or significantly reduce the detectable level of microorganism or antibodies against the microorganism in the patient's blood, serum, other bodily fluids, or tissues. The invention also includes using compounds of Formula I and Formula II in prophylactic therapies. In the context of prophylactic or preventative treatment a "therapeutically effective amount" is an amount sufficient to significantly decrease the treated human or non-human patient's risk of contracting a microorganism infection. A significant reduction is any detectable negative change that is statistically significant in a standard parametric test of statistical significance such as Student's T-test, where $p<0.05$.

Antimicrobial Compounds

For the purposes of this document, the following numbering system will apply to the core 1-thia-2,4a-diaza-cyclopenta[b]naphthalene-3,4-dione (when $A_1$=sulfur) structure or core 2H-isoxazolo[5,4-b]quinolizine-3,4-dione (when $A_1$=oxygen) structure. The numbers 1 through 9 refer specifically to positions within the tricyclic ring system whereas the letters A, B and C refer to the specific six (rings A and B) or five (ring C) member rings as shown below.

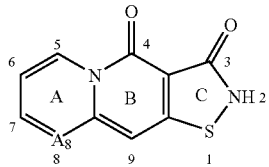

In addition to the compounds of Formula I and Formula II, described above the invention also includes compounds of Formula I and Formula II in which for the variables (e.g. $A_1$, $R_2$, $R_3$, $R_4$, etc.) one or more of the following conditions are met.

The $A_1$ variable (a). $A_1$ is Sulfur; e.g. the invention includes compounds of Formula III and Formula IV.

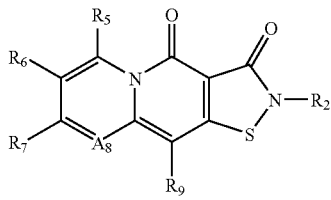
Formula III

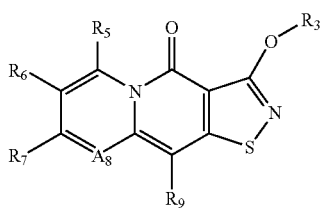
Formula IV (b). $A_1$ is SO; e.g. the invention includes compounds of Formula V and Formula VI.

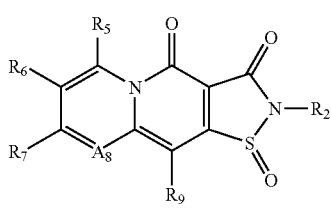
Formula V

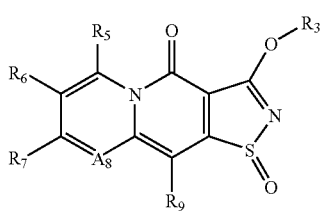
Formula VI (c). $A_1$ is $SO_2$; e.g. the invention includes compounds of Formula VII and Formula VIII.

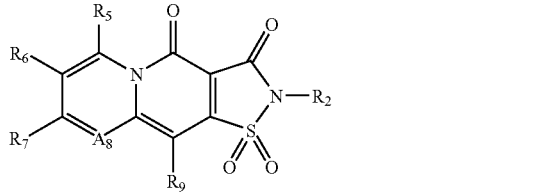
Formula VII

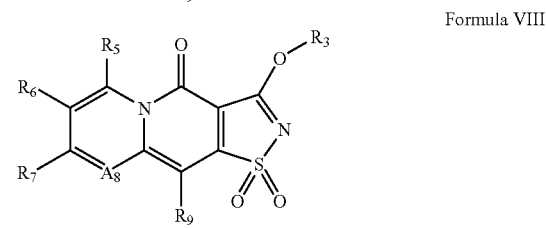
Formula VIII (d). $A_1$ is O; e.g. the invention includes compounds and salts of Formula IX and Formula X.

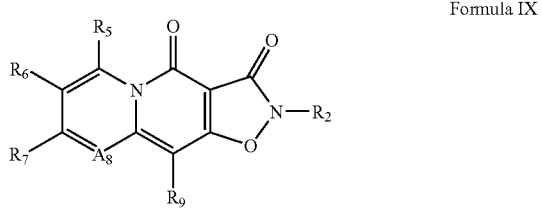
Formula IX

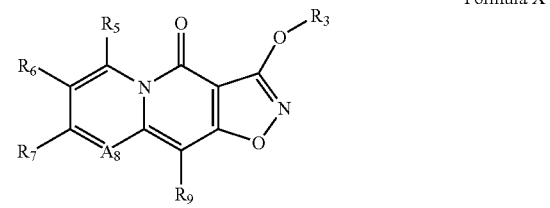
Formula X

The $R_2$ variable:

(a). The invention includes compounds of Formula I in which $R_2$ is hydrogen, or $R_2$ is $C_1$-$C_6$alkyl or ($C_3$-$C_7$cycloalkyl) $C_0$-$C_4$alkyl, each of which is substituted with at least one substituent chosen from hydroxy, amino, —COOH, —(C=O)$NR_{10}OR_{11}$, and —$CONH_2$; and is substituted with 0 to 3 substituents independently chosen from halogen, hydroxy, amino, cyano, nitro, —COOH, —$CONH_2$, $C_1$-$C_4$alkyl, $C_1$-$C_4$alkoxy, $C_1$-$C_2$haloalkyl, $C_1$-$C_2$haloalkoxy, and mono- and di-$C_1$-$C_4$alkylamino, and $C_2$-$C_4$alkanoyl.

(b). $R_2$ is hydrogen.

The $R_3$ variable:

(a). $R_3$ is $C_1$-$C_6$alkyl, $C_1$-$C_6$alkanoyl, mono- or di-$C_1$-$C_6$alkylcarbamate, or $C_1$-$C_6$alkylsulfonate; each of which is substituted with 0 to 3 substituents independently chosen from halogen, hydroxy, amino, cyano, nitro, $C_1$-$C_4$alkoxy, mono- and di-$C_1$-$C_4$alkylamino, $C_1$-$C_2$haloalkyl, and $C_1$-$C_2$haloalkoxy.

(b). $R_3$ is $C_1$-$C_6$alkyl or $C_1$-$C_6$alkanoyl, each of which is substituted with 0 to 3 substituents independently chosen from halogen, hydroxy, amino, cyano, $C_1$-$C_2$alkoxy, mono- and di-$C_1$-$C_2$alkylamino, $C_1$-$C_2$haloalkyl, and $C_1$-$C_2$haloalkoxy.

(c). $R_3$ is $C_1$-$C_6$alkyl or $C_1$-$C_6$alkanoyl.

(d). $R_3$ is hydrogen.

The $R_5$ variable:

(a). $R_5$ is hydrogen, amino, $C_1$-$C_2$alkyl, $C_1$-$C_2$alkoxy, mono- or di-($C_1$-$C_4$)alkylamino, or mono- or di-$C_1$-$C_4$ alkylhydrazinyl.

(b). $R_5$ is hydrogen, amino, mono- or di-($C_1$-$C_2$)alkylamino, or mono- or di-$C_1$-$C_2$ alkylhydrazinyl.

(c). $R_5$ is hydrogen.

The $R_6$ variable (a). $R_6$ is hydrogen, halogen, or amino.

(b). $R_6$ is fluoro or hydrogen.

The $R_7$ variable:

(a). $R_7$ is chloro, bromo, iodo, —O(SO$_2$)CF$_3$, or —N$_2$BF$_4$.

(b). $R_7$ is chloro.

(c). $R_7$ is $XR_A$ where X is absent, —CH$_2$—, —CH$_2$—CH$_2$—, —CH=CH—, or —C≡C—; and $R_A$ is $C_1$-$C_6$alkyl, $C_3$-$C_7$cycloalkyl, $C_3$-$C_7$cycloalkenyl, phenyl, a bicyclic 7- to 10-membered saturated, partially unsaturated, or aromatic carbocyclic group, a monocyclic or bicyclic 5- to 10-membered bicyclic saturated, partially unsaturated, or aromatic heterocylic group bound via a carbon atom; each of which $R_A$ is substituted with 0 to 5 substituents independently chosen from (i), (ii), and (iii).

(d). $R_7$ is $XR_A$ where X is absent, —CH$_2$—, —CH$_2$—CH$_2$—, —CH=CH—, or —C≡C—; and $R_A$ is a $C_1$-$C_6$alkyl, $C_3$-$C_7$cycloalkyl, $C_3$-$C_7$cycloalkenyl, phenyl, phenyl fused to a 5- or 6-membered heterocycloalkyl ring containing 1 or 2 nitrogen or oxygen atoms, indanyl naphthyl, dihydronaphthyl, tetrahydronapthyl, benz[b]thiophenyl, benzofuranyl, dihydroindolyl, dihydroisoindolyl, dihydroquinolinyl, dihydroisoquinolinyl, furanyl, indolyl, imidazolyl, isoindolyl, isoquinolinyl, isoxazolyl, piperazinyl, piperidinyl, pyrazinyl, pyridyl, pyrimidinyl, pyrrolidinyl, pyrrolyl, pyrazolyl, quinolinyl, quinazolinyl, quinoxalinyl, thienyl, thiazolyl, tetrahydropyridinyl, tetrahydroisoquionolinyl, or tetrahydroquinolinyl group; each of which is substituted with 0 to 5 substituents independently chosen from (i), (ii), and (iii).

(e). $R_7$ is $XR_A$ where X is absent, —CH$_2$—, —CH$_2$—CH$_2$—, —CH=CH—, or —C≡C—; and $R_A$ is $C_1$-$C_6$alkyl, $C_3$-$C_7$cycloalkyl, $C_3$-$C_7$cycloalkenyl, phenyl, phenyl fused to a 5- or 6-membered heterocycloalkyl ring containing 1 or 2 nitrogen or oxygen atoms, indanyl naphthyl, dihydronaphthyl, tetrahydronapthyl, benz[b]thiophenyl, benzofuranyl, dihydroindolyl, dihydroisoindolyl, dihydroquinolinyl, dihydroisoquinolinyl, furanyl, indolyl, imidazolyl, isoindolyl, isoquinolinyl, isoxazolyl, piperazinyl, piperidinyl, pyrazinyl, pyridyl, pyrimidinyl, pyrrolidinyl, pyrrolyl, pyrazolyl, quinolinyl, quinazolinyl, quinoxalinyl, thienyl, thiazolyl, tetrahydropyridinyl, tetrahydroisoquionolinyl, or tetrahydroquinolinyl; group; each of which is substituted with 0 to 5 substituents independently chosen from (i), (ii), and (iii), wherein (i) is chosen from halogen, hydroxy, amino, cyano, and nitro, (ii) is chosen from $C_1$-$C_4$alkyl, $C_2$-$C_4$alkenyl, $C_1$-$C_4$alkoxy, mono- and di-($C_1$-$C_4$)alkylamino, $C_1$-$C_2$haloalkyl, $C_1$-$C_2$haloalkoxy, ($C_3$-$C_7$cycloalkyl)$C_0$-$C_2$alkyl, ($C_3$-$C_7$cycloalkyl)$C_0$-$C_2$alkoxy, (phenyl)$C_0$-$C_2$alkyl, (phenyl)$C_0$-$C_2$alkoxy, (pyrrolidinyl)$C_0$-$C_2$alkyl, (piperidinyl)$C_0$-$C_2$alkyl, (piperazinyl)$C_0$-$C_2$alkyl, (morpholinyl)$C_0$-$C_2$alkyl, (thiomorpholinyl)$C_0$-$C_2$alkyl, pyridyl, pyrimidinyl, pyrazinyl, furanyl, benzofuranyl, pyrrolyl, pyrazolyl, imidazolyl, thienyl, $C_1$-$C_4$alkylthio, =NOR$_{10}$, —(C$_0$-$C_4$alkyl)(C=O)R$_{10}$, —(C$_0$-$C_4$alkyl)O(C=O)R$_{10}$, —(C$_0$-$C_4$alkyl)(C=O)NR$_{10}$R$_{11}$, —(C$_0$-$C_4$alkyl)O(C=O)NR$_{10}$R$_{11}$, —(C$_0$-$C_4$alkyl)(C=O)OR$_{10}$, —(C$_0$-$C_4$alkyl)NR$_{10}$(C=O)R$_{11}$, —(C$_0$-$C_4$alkyl)NR$_{10}$(C=O)OR$_{11}$, —(C$_0$-$C_4$alkyl)NR$_{10}$(C=O)NR$_{11}$R$_{12}$, —(C$_0$-$C_4$alkyl)NR$_{10}$(C=O)(C$_1$-$C_4$alkyl)NR$_{11}$(C=O)O—R$_{12}$, —(C$_0$-$C_4$alkyl)NR$_{10}$(C=S)NR$_{11}$R$_{12}$, —(C$_0$-$C_4$alkyl)NR$_{10}$NR$_{11}$R$_{12}$, —(C$_0$-$C_4$alkyl)N=NR$_{13}$, —(C$_0$-$C_4$alkyl)SO$_3$R$_{10}$, —(C$_0$-$C_4$alkyl)(S=O)OR$_{10}$, —(C$_0$-$C_4$alkyl)SO2R$_{13}$, —(C$_0$-$C_4$alkyl)SO2NR$_{10}$R$_{11}$, and —(C$_0$-$C_4$alkyl)NR$_{10}$SO$_2$R$_{13}$; and (iii) is chosen from —OR$_D$, —(C=O)R$_D$, —SO$_2$R$_D$, —SO$_3$R$_D$, and —NR$_{10}$SO$_2$R$_D$, where R$_D$ is $C_1$-$C_4$alkyl, ($C_3$-$C_7$cycloalkyl)$C_0$-$C_2$alkyl, (pyrrolidinyl)$C_0$-$C_2$alkyl, (piperidinyl)$C_0$-$C_2$alkyl, (piperazinyl)$C_0$-$C_2$alkyl, (morpholinyl)$C_0$-$C_2$alkyl, (thiomorpholinyl)$C_0$-$C_2$alkyl, (phenyl)$C_0$-$C_2$alkyl, (naphthyl)$C_0$-$C_2$alkyl, (pyridyl)$C_0$-$C_2$alkyl, (pyrimidinyl)$C_0$-$C_2$alkyl, (pyrazinyl)$C_0$-$C_2$alkyl, (furanyl)$C_0$-$C_2$alkyl, (benz[b]thiophenyl)$C_0$-$C_2$alkyl, (benzofuranyl)$C_0$-$C_2$alkyl, (quinolinyl)$C_0$-$C_2$alkyl, (isoquinolinyl)$C_0$-$C_2$alkyl, (quinazolinyl)$C_0$-$C_2$alkyl, (isoxazolyl)$C_0$-$C_2$alkyl, (indolyl)$C_0$-$C_2$alkyl, (dihydroindolyl)$C_0$-$C_2$alkyl, (pyrrolyl)$C_0$-$C_2$alkyl, (pyrazolyl)$C_0$-$C_2$alkyl, (imidazolyl)$C_0$-$C_2$alkyl, (thienyl)$C_0$-$C_2$alkyl, (isoindolyl)$C_0$-$C_2$alkyl, or (dihydroisoindolyl)$C_0$-$C_2$alkyl; where each of (ii) and (iii) is substituted with 0 to 3 substituents independently chosen from halogen, hydroxy, amino, cyano, nitro, oxo, —COOH, —CONH$_2$, $C_1$-$C_4$alkyl, $C_2$-$C_4$alkenyl, $C_2$-$C_4$alkynyl, $C_1$-$C_4$alkoxy, $C_1$-$C_4$alkoxycarbonyl, ($C_3$-$C_7$cycloalkyl)$C_0$-$C_4$alkyl, ($C_3$-$C_7$cycloalkyl)$C_0$-$C_4$alkoxy, mono- and di-($C_1$-$C_4$)alkylamino, $C_1$-$C_2$haloalkyl, $C_1$-$C_2$haloalkoxy, $C_2$-$C_4$alkanoyl, and phenyl.

(f) $R_7$ is $XR_A$ where X is absent, —CH$_2$—, —CH$_2$—CH$_2$—, —CH=CH—, or —C≡C—; and $R_A$ is a $C_1$-$C_6$alkyl, $C_3$-$C_7$cycloalkyl, $C_3$-$C_7$cycloalkenyl, phenyl, phenyl fused to a 5- or 6-membered heterocycloalkyl ring containing 1 or 2 nitrogen or oxygen atoms, indanyl naphthyl, dihydronaphthyl, tetrahydronapthyl, benz[b]thiophenyl, benzofuranyl, dihydroindolyl, dihydroisoindolyl, dihydroquinolinyl, dihydroisoquinolinyl, furanyl, indolyl, imidazolyl, isoindolyl, isoquinolinyl, isoxazolyl, piperazinyl, piperidinyl, pyrazinyl, pyridyl, pyrimidinyl, pyrrolidinyl, pyrrolyl, pyrazolyl, quinolinyl, quinazolinyl, quinoxalinyl, thienyl, thiazolyl, tetrahydropyridinyl, tetrahydroisoquionolinyl, or tetrahydroquinolinyl; group; each of which is substituted with 0 to 5 substituents independently chosen from (i), (ii), and (iii), wherein (i) is chosen from halogen, hydroxy, amino, cyano, and nitro, (ii) is chosen from $C_1$-$C_4$alkyl, $C_2$-$C_4$alkenyl, $C_1$-$C_4$alkoxy, mono- and di-($C_1$-$C_4$)alkylamino, $C_1$-$C_2$haloalkyl, $C_1$-$C_2$haloalkoxy, ($C_3$-$C_7$cycloalkyl)$C_0$-$C_2$alkyl, ($C_3$-$C_7$cycloalkyl)$C_0$-$C_2$alkoxy, (phenyl)$C_0$-$C_2$alkyl, (phenyl)$C_0$-$C_2$alkoxy, pyrrolidinyl, piperidinyl, piperazinyl, morpholinyl, thiomorpholinyl, pyridyl, thienyl, $C_1$-$C_4$alkylthio, —(C=O)OR$_{10}$, and —(C=O)NR$_{10}$R$_{11}$; and (iii) is chosen from —OR$_D$, —(C=O)R$_D$, —SO$_2$R$_D$, —SO$_3$R$_D$, and —NR$_{10}$SO$_2$R$_D$, where R$_D$ is $C_1$-$C_4$alkyl, ($C_3$-$C_7$cycloalkyl)$C_0$-$C_2$alkyl, piperidinyl, piperazinyl, phenyl, naphthyl, or pyridyl; where each of (ii) and (iii) is substituted with 0 to 3 substituents independently chosen from halogen, hydroxy, amino, cyano, nitro, oxo, —COOH, —CONH$_2$, $C_1$-$C_4$alkyl, $C_1$-$C_4$alkoxy, $C_1$-$C_4$alkoxycarbonyl, ($C_3$-$C_7$cycloalkyl)$C_0$-$C_2$alkyl, mono- and di-($C_1$-$C_4$)alkylamino, $C_1$-$C_2$haloalkyl, $C_1$-$C_2$haloalkoxy, $C_2$-$C_4$alkanoyl, and phenyl.

(g). $R_7$ is $XR_A$ where X is absent, —$CH_2$—, —$CH_2$—$CH_2$—, —CH=CH—, or —C≡C—; and $R_A$ is a $C_1$-$C_6$alkyl, $C_3$-$C_7$cycloalkyl, $C_3$-$C_7$cycloalkenyl, phenyl, phenyl fused to a 5- or 6-membered heterocycloalkyl ring containing 1 or 2 nitrogen or oxygen atoms, indanyl naphthyl, dihydronaphthyl, tetrahydronapthyl, benz[b]thiophenyl, benzofuranyl, dihydroindolyl, dihydroisoindolyl, dihydroquinolinyl, dihydroisoquinolinyl, furanyl, indolyl, imidazolyl, isoindolyl, isoquinolinyl, isoxazolyl, piperazinyl, piperidinyl, pyrazinyl, pyridyl, pyrimidinyl, pyrrolidinyl, pyrrolyl, pyrazolyl, quinolinyl, quinazolinyl, quinoxalinyl, thienyl, thiazolyl, tetrahydropyridinyl, tetrahydroisoquionolinyl, or tetrahydroquinolinyl; group; each of which is substituted with 0 to 5 substituents independently chosen from halogen, hydroxy, amino, cyano, nitro, $C_1$-$C_4$alkyl, $C_2$-$C_4$alkenyl, $C_1$-$C_4$alkoxy, mono- and di-($C_1$-$C_4$)alkylamino, $C_1$-$C_2$haloalkyl, $C_1$-$C_2$haloalkoxy, ($C_3$-$C_7$cycloalkyl)$C_0$-$C_2$alkyl, ($C_3$-$C_7$cycloalkyl)$C_0$-$C_2$alkoxy, (phenyl)$C_0$-$C_2$alkyl, (phenyl)$C_0$-$C_2$alkoxy, pyrrolidinyl, piperidinyl, piperazinyl, morpholinyl, thiomorpholinyl, pyridyl, thienyl, $C_1$-$C_4$alkylthio, —(C=O)$OR_{10}$, —(C=O)$NR_{10}R_{10}$; and —$OR_D$, —(C=O)$R_D$, —$SO_2R_D$, —$SO_3R_D$, and —$NR_{10}SO_2R_D$, where $R_D$ is $C_1$-$C_4$alkyl, piperidinyl, phenyl, naphthyl, and pyridyl; and each $R_D$ is substituted with 0 to 3 substituents independently chosen from halogen, hydroxy, amino, cyano, $C_1$-$C_2$alkyl, $C_1$-$C_2$alkoxy, mono- and di-($C_1$-$C_2$)alkylamino, $C_1$-$C_2$haloalkyl, and $C_1$-$C_2$haloalkoxy.

(h) $R_7$ is $XR_A$ where X is absent and $R_A$ carries the definition set forth in (f) or (g) above.

(i) $R_7$ is $XR_A$ where X is absent, —$CH_2$—, —$CH_2$—$CH_2$—, —CH=CH—, or —C≡C—; or in certain embodiments X is absent, and $R_A$ is phenyl or pyridyl, each of which is substituted with 0 to 3 substituents independently chosen from halogen, hydroxy, amino, cyano, nitro, $C_1$-$C_4$alkyl, $C_2$-$C_4$alkenyl, $C_1$-$C_4$alkoxy, mono- and di-($C_1$-$C_4$)alkylamino, $C_1$-$C_2$haloalkyl, $C_1$-$C_2$haloalkoxy, ($C_3$-$C_7$cycloalkyl)$C_0$-$C_2$alkyl, ($C_3$-$C_7$cycloalkyl)$C_0$-$C_2$alkoxy, (phenyl)$C_0$-$C_2$alkyl, (phenyl)$C_0$-$C_2$alkoxy, pyrrolidinyl, piperidinyl, piperazinyl, morpholinyl, thiomorpholinyl, pyridyl, thienyl, $C_1$-$C_4$alkylthio, —(C=O)$OR_{10}$, and —(C=O)$NR_{10}R_{11}$; and substituted with 1 or 2 substituents independently chosen from —$OR_D$, —(C=O)$R_D$, —$SO_2R_D$, —$SO_3R_D$, and —$NR_{10}SO_2R_D$, where $R_D$ is $C_1$-$C_4$alkyl, piperidinyl, phenyl, naphthyl, or pyridyl; and each $R_D$ is substituted with 0 to 3 substituents independently chosen from halogen, hydroxy, amino, cyano, $C_1$-$C_2$alkyl, $C_1$-$C_2$alkoxy, mono- and di-($C_1$-$C_2$)alkylamino, $C_1$-$C_2$haloalkyl, and $C_1$-$C_2$haloalkoxy.

(j) $R_7$ is $XR_A$ where X is absent and $R_A$ is a phenyl, pyridyl, pyrimidinyl, furanyl, isoquinolinyl, quinolinyl, indolyl, pyrrolyl, isoindolyl, dihydroisoindolyl, tetrahydroisoquinolinyl, tetrahydroisoquinolinyl, or thienyl group, each of which is substituted with 0 to 3 substituents independently chosen from halogen, hydroxy, amino, cyano, $C_1$-$C_4$alkyl, $C_1$-$C_4$alkoxy, mono- and di-($C_1$-$C_4$)alkylamino, $C_1$-$C_2$haloalkyl, and $C_1$-$C_2$haloalkoxy.

(k) $R_7$ is $XR_A$ where X is absent and $R_A$ is phenyl, pyrid-3-yl, pyrid-4-yl, pyrimidin-5-yl, furan-3-yl, quinolin-3-yl, quinolin-5-yl, quinolin-6-yl, isoindol-5-yl, tetrahydroisoquinolin-5-yl, tetrahydroisoquinolin-6-yl, tetrahydroisoquinolin-7-yl, tetrahydroisoquinolin-8-yl, or indol-5-yl, each of which is substituted with 0 to 2 substituents independently chosen from halogen, hydroxy, amino, $C_1$-$C_2$alkyl, and $C_1$-$C_2$alkoxy.

(l) $R_7$ is $XR_A$ where X is absent and $R_A$ is phenyl, pyridyl-3-yl or pyrid-4-yl, each of which is substituted with 1 or 2 substituents independently chosen from fluoro, amino, hydroxy, cyano, and methyl.

(m) $R_7$ is $XR_A$ where X is absent and $R_A$ is tetrahydroisoquinolin-5-yl, tetrahydroisoquinolin-6-yl, tetrahydroisoquinolin-7-yl, or tetrahydroisoquinolin-8-yl, each of which is substituted with 0 to 3 substituents independently chosen from $C_1$-$C_3$alkyl.

(n) $R_7$ is $XR_A$ where X is absent and $R_A$ is tetrahydroisoquinolin-6-yl optionally substituted at each of the 1, 2, and 3 positions with methyl.

(o) $R_7$ is $XR_A$ where X is absent and $R_A$ is isoindol-5-yl substituted with 0 to 3 independently chosen $C_1$-$C_3$alkyl substituents.

(p) $R_7$ is $XR_A$ where X is absent and $R_A$ is isoindol-5-yl optionally substituted at each of the 1, 2, or 3 positions with methyl.

(q) $R_7$ is $XR_A$ where X is absent, —$CH_2$—, —$CH_2$—$CH_2$—, —CH=CH—, or —C≡C—; or in certain embodiments X is absent, and $R_A$ is phenyl fused to a 5- or 6-membered heterocycloalkyl ring containing 1 or 2 nitrogen or oxygen atoms, where $R_A$ is substituted with 0 to 3 substituents independently chosen from (i), (ii), and (iii).

(r) $R_7$ is $XR_A$ where X is absent, —$CH_2$—, —$CH_2$—$CH_2$—, —CH=CH—, or —C≡C—; or in certain embodiments X is absent, $R_A$ is phenyl fused to a 5- or 6-membered heterocycloalkyl ring containing 1 or 2 nitrogen or oxygen atoms, where $R_D$ is substituted with 0 to 2 substituents independently chosen from halogen, hydroxy, amino, $C_1$-$C_2$alkyl, and $C_1$-$C_2$alkoxy.

The $A_8$ variable
(a). $A_8$ is nitrogen.
(b). $A_8$ is $CR_8$.
(c). $A_8$ is $CR_8$ and $R_8$ is hydrogen, halogen, $C_1$-$C_2$alkyl, $C_1$-$C_2$alkoxy, trifluoromethyl, or trifluoromethoxy.
(d). $A_8$ is $CR_8$ and $R_8$ is hydrogen or methyl.

The $R_9$ variable:
(a). $R_9$ is $C_1$-$C_8$alkyl, $C_1$-$C_4$alkoxy, mono- or di-($C_1$-$C_4$)alkylamino, $C_2$-$C_4$alkanoyl, $C_1$-$C_2$haloalkyl, $C_1$-$C_2$haloalkoxy, ($C_3$-$C_7$cycloalkyl)$C_0$-$C_4$alkyl, or phenyl, each of which is substituted with 0 to 3 substituents independently chosen from hydroxy, amino, $C_1$-$C_2$alkyl, $C_1$-$C_2$alkoxy, mono- and di-($C_1$-$C_2$)alkylamino, $C_1$-$C_2$haloalkyl, and $C_1$-$C_2$haloalkoxy.

(b). $R_9$ is $C_1$-$C_4$alkyl, cyclopropyl, or phenyl, each of which is substituted with 0 to 3 substituents independently chosen from halogen, hydroxy, amino, $C_1$-$C_2$alkyl, $C_1$-$C_2$alkoxy, mono- and di-($C_1$-$C_2$)alkylamino, $C_1$-$C_2$haloalkyl, and $C_1$-$C_2$haloalkoxy.

(c). $R_9$ is $C_1$-$C_4$alkyl or cyclopropyl, or $R_9$ is phenyl substituted with 2 substituents chosen from halogen, hydroxy, amino, $C_1$-$C_2$alkyl, $C_1$-$C_2$alkoxy, mono- and di-($C_1$-$C_2$)alkylamino, $C_1$-$C_2$haloalkyl, and $C_1$-$C_2$haloalkoxy.

(d). $R_9$ is ethyl, t-butyl, cyclopropyl, or 2,4-difluorophenyl.
(e). $R_9$ is cyclopropyl.

The invention includes compounds of Formula I and Formula II in which the variables $A_1$, $R_2$, $R_3$, $R_5$, $R_6$, $R_7$, $A_8$, and $R_9$ carry any combination of the definitions set forth for these variables above that results in a stable compound.

Certain compounds of Formula I and Formula II exhibit potent antibacterial, antifungal, and/or antiprotozoal activity. Particular compounds of the invention exhibit Minimum Inhibitory Concentrations (MIC) of 64 µg/ml or less against *Staphyloccocus aureus* and/or *Eschericia coli* in a standard assay for determining the MIC of a compound against these bacteria, such as the assay provided in Example 9 below.

Preferred compounds of Formula I and II exhibit MIC values of 10 μg/ml or less against *Staphyloccocus aureus* and/or *Eschericia coli*. More preferred compound of the Formula I and II exhibit MIC values of 4 μg/ml or less, or even more preferably 1 μg/ml or less, against *Staphyloccocus aureus* and/or *Eschericia coli*.

Certain compounds of Formula I and Formula II are selective antimicrobial agents; having the ability to kill or inhibit the growth or reproduction of pathogenic microbial organisms, while having little or no effect on the cells of fish, amphibians, reptiles, birds, or mammals. The selectivity of compounds of Formula I and Formula II may be assessed by determining the $CC_{50}$ (the concentration at which 50% of the cells are killed) for cultured cells of a higher animal, such as a fish, reptiles, amphibian, bird, or mammal. Certain compounds of the invention exhibit a $CC_{50}$ of greater that 100 micromolar for mammalian cells. Certain compounds of the invention exhibit a CC50 of greater than 100 micromolar for cultured human hepatocytes, and also exhibit MIC values of 64 μg/ml or less, preferably 10 μg/ml or less, or more preferably 4 μg/ml or less, or still more preferably 1 μg/ml or less against *Staphyloccocus aureus* and/or *Eschericia coli*.

Without wishing to be bound to any particular theory it is believed that the antimicrobial properties of compounds of Formula I and Formula II are due to the ability to these compounds to inhibit the activity of microbial DNA gyrases while having little or no effect on the analogous enzyme, Topoisomerase II, present in higher organisms. Certain preferred compounds of the invention are 100-fold or more selective for bacterial DNA gyrases than for mammalian, particularly human, Topoisomerase II.

Synthetic Intermediates

The invention includes novel intermediates useful for the synthesis of antimicrobial compounds of Formula I and Formula II. Coupling reactions occur between R'-M and R"-Y in the presence of catalyst Q, where M is Li, Mg, B, Al, Si, Zn, Cu, Zr, or Sn; where Y is I, Br, Cl, —O(SO₂)CF₃, or —N₂BF₄; Q is Fe, Ni, Cu, Pd, or Rh; and R' and R" are organic molecules to which M and Y are bound. M may also be Boron, disubstituted with OH, OG, or G, where G is an optionally substituted straight, branched, or cyclic alkyl group, or other suitable group; Y is Br, and where Q is Pd. A general review of this chemistry can be found in Tamao, K and Miyaura, N. Topics in Current Chemistry 219: 1-9 (2002). A review of the use of coupling reagents in which M is Boron with a listing of potential boronates, palladium catalysts, and reaction conditions can be found in Miyaura, N. Topics in Current Chemistry 219: 11-59 (2002).

Thus the invention includes intermediates of Formula XI and Formula XII:

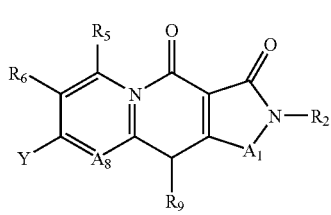

Formula XI

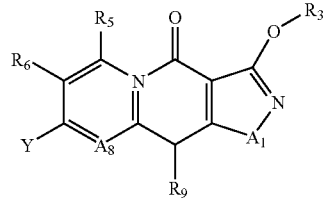

Formula XII

Wherein $A_1$, $A_8$, $R_2$, $R_3$, $R_5$, $R_6$, and $R_9$ carry the definitions set forth above and Y is I, Br, Cl, —O(SO₂)CF₃, or —N₂BF₄. Here compounds of Formula XI and Formula XII play the role of R"—Y intermediate in the coupling reaction between R'-M and R"—Y. These intermediates are coupled to compounds of the Formula R'-M where R' is a group R.

R is $XR_4$ where X is absent, —CH₂—CH₂—, —CH═CH—, —(C═O)—, —(C═ONH)—, or —C≡C—, and $R_4$ is $C_1$-$C_6$alkyl, $C_3$-$C_7$cycloalkyl, $C_3$-$C_7$cycloalkenyl, phenyl, a bicyclic 7- to 10-membered saturated, partially unsaturated, or aromatic carbocyclic group, a monocyclic or bicyclic a 5- to 10-membered bicyclic saturated, partially unsaturated, or aromatic heterocyclic group bound via a carbon atom; each of which $R_4$ is substituted with 0 to 5 substituents independently chosen from (i), (ii), and (iii); where (i) is chosen from halogen, hydroxy, amino, cyano, and nitro, (ii) is chosen from $C_1$-$C_6$alkyl, $C_2$-$C_6$alkenyl, $C_2$-$C_6$alkynyl, ($C_1$-$C_6$alkoxy)$C_0$-$C_4$alkyl, mono- and di-($C_1$-$C_4$)alkylamino, $C_1$-$C_2$haloalkyl, $C_1$-$C_2$haloalkoxy, ($C_3$-$C_7$cycloalkyl)$C_0$-$C_4$carbohydryl, ($C_3$-$C_7$cycloalkyl)$C_0$-$C_4$carbohydryl-O—, ($C_4$-$C_7$cycloalkenyl)$C_0$-$C_4$carbohydryl, (aryl)$C_0$-$C_6$carbohydryl, (aryl)$C_1$-$C_4$alkoxy, ($C_2$-$C_6$heterocycloalkyl)$C_0$-$C_4$carbohydryl, (heteroaryl)$C_0$-$C_6$carbohydryl, $C_1$-$C_6$alkylthio, ═NOR₁₀, ═NR₁₀, —(C₀-C₄alkyl)(C═O)R₁₀, —(C₀-C₄alkyl)O(C═O)R₁₀, —(C₀-C₄alkyl)(C═O)NR₁₀R₁₁, —(C₀-C₄alkyl)O(C═O)NR₁₀R₁₀, —(C₀-C₄alkyl)(C═O)OR₁₀, —(C₀-C₄alkyl)NR₁₀(C═O)R₁₁, —(C₀-C₄alkyl)NR₁₀(C═O)OR₁₁, —(C₀-C₄alkyl)NR₁₀(C═O)NR₁₁R, —(C₀-C₄alkyl)NR₁₀(C═O)(C₁-C₄alkyl)NR₁₁(C═O)O—R₁₂, —(C₀-C₄alkyl)NR₁₀(C═S)NR₁₁R₁₂, —(C₀-C₄alkyl)NR₁₀NR₁₁R₁₂, —(C₀-C₄alkyl)N═NR₁₃, —(C₀-C₄alkyl)SO₃R₁₀, —(C₀-C₄alkyl)(S═O)OR₁₀, —(C₀-C₄alkyl)SO₂R₁₃, —(C₀-C₄alkyl)SO2NR₁₀R₁₁, and —(C₀-C₄alkyl)NR₁₀SO₂R₁₃; and (iii) is chosen from —OR_D, —(C═O)RD, —SO₂RD, —SO₃RD, —NR₁₀SO2RD, where RD is C1-C4alkyl, ($C_3$-$C_7$cycloalkyl)$C_0$-$C_2$alkyl, (C2-C6heterocycloalkyl)$C_0$-$C_2$alkyl, (aryl)$C_0$-$C_2$alkyl, and (heteroaryl)$C_0$-$C_2$alkyl;

where each of (ii) and (iii) is substituted with 0 to 3 substituents independently chosen from halogen, hydroxy, amino, cyano, nitro, oxo, —COOH, —CONH2, C1-C4alkyl, C2-C4alkenyl, C2-C4alkynyl, C1-C4alkoxy, C1-C4alkoxycarbonyl, ($C_3$-$C_7$cycloalkyl)$C_0$-$C_4$carbohydryl, ($C_3$-$C_7$cycloalkyl)$C_0$-$C_4$alkoxy, mono- and di-(C1-C4)alkylamino, $C_1$-$C_2$haloalkyl, $C_1$-$C_2$haloalkoxy, C2-C4alkanoyl and phenyl.

M is Li, Mg, B, Al, Si, Zn, Cu, Zr, or Sn; or M is Boron, disubstituted with OH, OG, or G, where G is an optionally substituted straight, branched, or cyclic alkyl group, an optionally substituted aryl or arylalkyl group, or other suitable group.

The invention also includes intermediates of Formula XIII and Formula XIV.

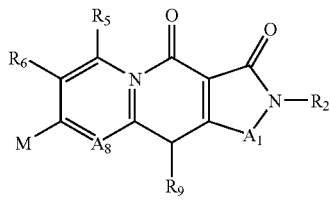

Formula XIII

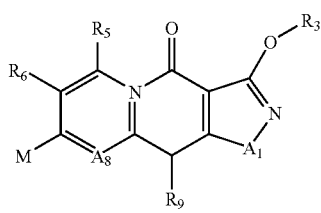

Formula XIV

In Formula XIII and XIV $A_1$, $A_8$, $R_2$, $R_3$, $R_5$, $R_6$, and $R_9$ carry the definitions set forth above and M is Li, Mg, B, Al, Si, Zn, Cu, Zr, or Sn; or M is Boron, disubstituted with OH, OG, or G, where G is an optionally substituted straight, branched, or cyclic alkyl group, an optionally substituted aryl or arylalkyl group, or other suitable group. Here compounds of Formula XIII and Formula XIV play the role of R'-M in the coupling reaction. These intermediates are coupled to compounds of the Formula R"-Y where Y is I, Br, Cl, —O(SO$_2$)CF$_3$, or —N$_2$BF$_4$ and R" carries the definition set forth above for R.

Pharmaceutical Preparations

Compounds and salts of Formula I and Formula II can be administered as the neat chemical, but are preferably administered as a pharmaceutical composition or formulation. Accordingly, the invention provides pharmaceutical formulations comprising a compound or pharmaceutically acceptable salt of Formula I or Formula II, together with one or more pharmaceutically acceptable carrier, excipients, adjuvant, diluent, or other ingredient.

Compounds of general Formula I and Formula II may be administered orally, topically, parenterally, by inhalation or spray, sublingually, transdermally, via buccal administration, rectally, as an ophthalmic solution, or by other means, in dosage unit formulations containing conventional non-toxic pharmaceutically acceptable carriers, excipients, adjuvants, and vehicles.

In addition to the subject compound, the compositions of the invention may contain a pharmaceutically acceptable carrier, one or more compatible solid or liquid filler, diluents or encapsulating substances, which are suitable for administration to an animal. Carriers must be of sufficiently high purity and sufficiently low toxicity to render them suitable for administration to the animal being treated. The carrier can be inert or it can possess pharmaceutical benefits of its own. The amount of carrier employed in conjunction with the compound is sufficient to provide a practical quantity of material for administration per unit dose of the compound.

Exemplary pharmaceutically acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, and corn oil; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

In particular, pharmaceutically acceptable carriers for systemic administration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred carriers for parenteral administration include propylene glycol, ethyl oleate, pyrrolidone, ethanol, and sesame oil.

Optional active agents may be, included in a pharmaceutical composition, which do not substantially interfere with the activity of the compound of the present invention.

Effective concentrations of one or more of the compounds of the invention including pharmaceutically acceptable salts, esters or other derivatives thereof are mixed with a suitable pharmaceutical carrier, excipients, adjuvant, or vehicle. In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as Tween, or dissolution in aqueous sodium bicarbonate. Derivatives of the compounds, such as salts of the compounds or prodrugs of the compounds may also be used in formulating effective pharmaceutical compositions.

Upon mixing or addition of the compound(s) of Formula I and/or Formula II, the resulting mixture may be a solution, suspension, emulsion or the like. The form of the resulting mixture depends upon a number of factors, including the intended mode of administration and the solubility of the compound in the chosen carrier or vehicle. The effective concentration sufficient for ameliorating the symptoms of the disease, disorder or condition treated and may be empirically determined.

The pharmaceutical compositions containing compounds of general Formula I and/or Formula II may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents, such as sweetening agents, flavoring agents, coloring agents and preserving agents, in order to provide pharmaceutically elegant and palatable preparations.

Oral formulations contain between 0.1 and 99% of a compound of the invention and usually at least about 5% (weight %) of a compound of the present invention. Some embodiments contain from about 25% to about 50% or from 5% to 75% of a compound of invention.

Liquids Formulations

Compounds of the invention can be incorporated into oral liquid preparations such as aqueous or oily suspensions, solutions, emulsions, syrups, or elixirs, for example. Moreover, formulations containing these compounds can be presented as a dry product for constitution with water or other suitable vehicle before use. Such liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monsoleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid).

Orally administered compositions also include liquid solutions, emulsions, suspensions, powders, granules, elixirs, tinctures, syrups, and the like. The pharmaceutically acceptable carriers suitable for preparation of such compositions are well known in the art. Oral formulations may contain preservatives, flavoring agents, sweetening agents, such as sucrose or saccharin, taste-masking agents, and coloring agents.

Typical components of carriers for syrups, elixirs, emulsions and suspensions include ethanol, glycerol, propylene glycol, polyethylene glycol, liquid sucrose, sorbitol and water. Syrups and elixirs may be formulated with sweetening agents, for example glycerol, propylene glycol, sorbitol or sucrose. Such formulations may also contain a demulcent.

Suspensions

For a suspension, typical suspending agents include methylcellulose, sodium carboxymethyl cellulose, Avicel RC-591, tragacanth and sodium alginate; typical wetting agents include lecithin and polysorbate 80; and typical preservatives include methyl paraben and sodium benzoate.

Aqueous suspensions contain the active material(s) in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents; may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol substitute, or condensation products of ethylene oxide with partial esters derived from fatty acids and hexitol anhydrides, for example polyethylene sorbitan substitute. The aqueous suspensions may also contain one or more preservatives, for example ethyl, or n- propyl p-hydroxybenzoate.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Emulsions

Pharmaceutical compositions of the invention may also be in the form of oil-in-water emulsions. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate.

Dispersible Powders

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Tablets and Capsules

Tablets typically comprise conventional pharmaceutically compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules (including time release and sustained release formulations) typically comprise one or more solid diluents disclosed above. The selection of carrier components often depends on secondary considerations like taste, cost, and shelf stability.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit coatings, waxes and shellac.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Injectable and Parenteral Formulations

Pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid are useful in the preparation of injectables.

Compounds of Formula I and Formula II may be administered parenterally in a sterile medium. Parenteral administration includes subcutaneous injections, intravenous, intramuscular, intrathecal injection or infusion techniques. The drug, depending on the vehicle and concentration used, can either be suspended or dissolved in the vehicle. Advantageously, adjuvants such as local anesthetics, preservatives and buffering agents can be dissolved in the vehicle. In compositions for parenteral administration the carrier comprises at least about 90% by weight of the total composition.

Suppositories

Compounds of Formula I and Formula II may also be administered in the form of suppositories for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Topical Formulations

Compounds of the invention may be formulated for local or topical application, such as for topical application to the skin and mucous membranes, such as in the eye, in the form of gels, creams, and lotions and for application to the eye or for intracisternal or intraspinal application. Topical compositions of the present invention may be in any form including, for example, solutions, creams, ointments, gels, lotions, milks, cleansers, moisturizers, sprays, skin, patches, and the like.

Such solutions may be formulated as 0.01%-10% isotonic solutions, pH about 5-7, with appropriate salts. Compounds of the invention may also be formulated for transdermal administration as a transdermal patch.

Topical compositions containing the active compound can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like.

Other materials suitable for use in topical carriers include, for example, emollients, solvents, humectants, thickeners and powders. Examples of each of these types of materials, which can be used singly or as mixtures of one or more materials, are as follows:

Emollients, such as stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, iso-propyl myristate, iso-propyl palmitate, iso-propyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, and myristyl myristate; propellants, such as propane, butane, isobutane, dimethyl ether, carbon dioxide, and nitrous oxide; solvents, such as ethyl alcohol, methylene chloride, iso-propanol, castor oil, ethylene glycol monoethyl ether, diethylene glycol monobutyl ether, diethylene glycol monoethyl ether, dimethyl sulphoxide, dimethyl formamide, tetrahydrofuran; humectants, such as glycerin, sorbitol, sodium 2-pyrrolidone-5-carboxylate, soluble collagen, dibutyl phthalate, and gelatin; and powders, such as chalk, talc, fullers earth, kaolin, starch, gums, colloidal silicon dioxide, sodium polyacrylate, tetra alkyl ammonium smectites, trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, and ethylene glycol monostearate.

The compounds of the invention may also be topically administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Other Formulations

Other compositions useful for attaining systemic delivery of the subject compounds include sublingual, buccal and nasal dosage forms. Such compositions typically comprise one or more of soluble filler substances such as sucrose, sorbitol and mannitol, and binders such as acacia, microcrystalline cellulose, carboxymethyl cellulose and hydroxypropyl methylcellulose. Glidants, lubricants, sweeteners, colorants, antioxidants and flavoring agents disclosed above may also be included.

Compositions for inhalation typically can be provided in the form of a solution, suspension or emulsion that can be administered as a dry powder or in the form of an aerosol using a conventional propellant (e.g., dichlorodifluoromethane or trichlorofluoromethane).

Additional Components

The compositions of the present invention may also optionally comprise an activity enhancer. The activity enhancer can be chosen from a wide variety of molecules that function in different ways to enhance antimicrobial effects of compounds of the present invention. Particular classes of activity enhancers include skin penetration enhancers and absorbtion enhancers.

Pharmaceutical compositions of the invention may also contain additional active agents can be chosen from a wide variety of molecules, which can function in different ways to enhance the antimicrobial or therapeutic effects of a compound of the present invention. These optional other active agents, when present, are typically employed in the compositions of the invention at a level ranging from about 0.01% to about 15%. Some embodiments contain from about 0.1% to about 10% by weight of the composition. Other embodiments contain from about 0.5% to about 5% by weight of the composition.

Packaged Formulations

The invention includes packaged pharmaceutical formulations. Such packaged formulations include a pharmaceutical composition containing one or more compounds or salts of Formula I in a container and instructions for using the composition to treat an animal (typically a human patient) suffering from a microorganism infection) or prevent a microorganism infection in an animal.

In all of the foregoing the compounds of the invention can be administered alone or as mixtures, and the compositions may further include additional drugs or excipients as appropriate for the indication.

Methods of Treatment

The invention includes methods of preventing and treating microorganism infections, particularly bacterial and protozoal infections, by administering a therapeutically effective amount of one or more compounds of Formula I and of Formula II to an animal at risk for a microorganism infection or having a microorganism infection. The animal may be a fish, amphibian, reptile or bird, but is preferably a mammal. Methods of treating and preventing microorganism infections in livestock animals, companion animals, and human patients are particularly preferred.

The compounds disclosed herein are useful for preventing and treating bacterial infections in animals. Furthermore compounds of the invention may be used to treat a variety of conditions not attributed to bacterial infections. These include diseases and disorders caused fungal infections, mycoplasma infections, protozoal infections, or other conditions involving infectious organisms.

In some circumstances an effective amount of a compound of Formula I or Formula II may be an amount sufficient to reduce the symptoms of the microorganism infection. Alternatively an effective amount of a Compound of Formula I may be an amount sufficient to significantly reduce the amount of microorganism or antibodies against the detectable in a patient's tissues or bodily fluids.

Methods of treatment also include inhibiting microorganism replication in vivo, in an animal at risk for a microorganism infection or suffering from such an infection, by administering a sufficient concentration of a compound of Formula I or Formula II to inhibit bacterial survival in vitro. By "sufficient concentration" of a compound administered to the patient is meant the concentration of the compound available in the animal's system to prevent or combat the infection. Such a concentration by be ascertained experimentally, for example by assaying blood concentration of the compound, or theoretically, by calculating bioavailability. The amount of a compound sufficient to inhibit bacterial survival in vitro may be determined with a conventional assay for bacterial survival such as the Minimum Inhibitory Concentration (MIC) Assay disclosed in Example 9, which follows.

The invention also includes using compounds of Formula I and Formula II in prophylactic therapies. In the context of prophylactic or preventative treatment an effective amount of a compound of the invention is an amount sufficient to significantly decrease the treated animal's risk of contracting a microorganism infection.

Compounds of the invention are particularly useful for treating and preventing infectious disorders. These include for example: ocular infections such as conjunctivitis; urinary tract and genital infections, such as complicated urinary tract infections, acute urinary tract and genital infections, such as pyelonephritis, cervical gonococcal infections, cystitis, urethral chlamydial infections, cervical chlamydial infections, urethral gonococcal infections, and prostatitis, respiratory infections, such as lower respiratory tract infections, acute sinusitis, acute exacerbations of chronic bronchitis, community-acquired pneumonia, and nosocomial pneumonia, skin infections, such as skin-structure infections, impetigo, folliculitis, boils, scalded skin syndrome, and cellulites, and other infections such as bone infections, joint infections, infectious diarrhea, typhoid fever, intra-abdominal infections, gynecologic infections, including toxic shock syndrome, pelvic infections, and post-surgical infections.

The disclosed compounds are useful for treating infections caused by the following microorganisms:

Aerobic Gram-positive Microorganisms: Including but not limited to *Enterococcus faecalis, Enterococcus faecium, Staphylococcus aureus, Staphylococcus epidermidis, Staphylococcus saprophyticus, Streptococcus pneumoniae, Streptococcus pyogenes, Staphylococcus haemolyticus,* and *Staphylococcus hominis.*

Aerobic Gram-negative Microorganisms: Including but not limited to *Campylobacter jejuni, Citrobacter diversus, Citrobacter freundii, Enterobacter cloacae, Escherichia coli, Haemophilus influenzae, Haemophilus parainfluenzae, Klebsiella pneumoniae, Moraxella catarrhalis, Morganella morganii, Neisseria gonorrhoeae, Proteus mirabilis, Proteus vulgaris, Providencia rettgeri, Providencia stuartii, Pseudomonas aeruginosa, Stenotrophomonas maltophila, Salmonella typhi, Serratia marcescens, Shigella boydii, Shigella dysenteriae, Shigella flexneri, Shigella sonnei. Acinetobacter Iwoffi, Aeromonas hydrophila, Edwardsiella tarda, Enterobacter aerogenes, Klebsiella oxytoca, Legionella pneumophila, Pasteurella multocida, Salmonella enteritidis, Vibrio cholerae, Vibrio parahaemolyticus, Vibrio vulnificus, Yersinia enterocolitica* and *H. Pylorii.*

Non-bacterial microorganisms: *Mycoplasma, Legionella* and *Chlamydia.*

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most infectious disorders, a dosage regimen of 4 times daily or less is preferred and a dosage regimen of 1 or 2 times daily is particularly preferred.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Combination Administration

The compounds of the invention may also be useful in combination with other pharmaceutically active agents such as antibacterial agents, antiviral agents, antifungal agents, anti-inflammatories, interferon, efflux-pump inhibitors, and beta-lactamase inhibitors. Antibiotic agents include any molecule that tends to prevent, inhibit or destroy life and as such, includes anti-bacterial agents, anti-fungicides, anti-viral agents, and anti-parasitic agents.

A composition comprising a compound or salt of Formula I or Formula II in combination with one or more other antibacterial agent, antiprotozoal agent, antifungal agent, antiviral agent, interferon, efflux-pump inhibitor, or beta-lactamase inhibitor is provided herein.

Pharmaceutical compositions of the invention include single dosage forms containing of a compound of Formula I and/or Formula II and one or more other active agent, dosage forms containing more than one compound of Formula I and/or Formula II, and separate. administration of a compound of Formula I and/or Formula II with another active agent.

The following active agents, which are useful in combinations of the invention, may be isolated from an organism that produces the agent or synthesized by methods known to those of ordinary skill in the art of medicinal chemistry or purchased from a commercial source.

Anti-bacterial antibiotic agents include, but are not limited to, penicillins, cephalosporins, carbacephems, cephamycins, carbapenems, monobactams, aminoglycosides, glycopeptides, quinolones, tetracyclines, macrolides, and fluoroquinolones (see Table below). Examples of antibiotic agents include, but are not limited to, Penicillin G (CAS Registry No.: 61-33-6); Methicillin (CAS Registry No.: 61-32-5); Nafcillin (CAS Registry No.: 147-52-4); Oxacillin (CAS Registry No.: 66-79-5); Cloxacillin (CAS Registry No.: 61-72-3); Dicloxacillin (CAS Registry No.: 3116-76-5); Ampicillin (CAS Registry No.: 69-53-4); Amoxicillin (CAS Registry No.: 26787-78-0); Ticarcillin (CAS Registry No.: 34787-01-4); Carbenicillin (CAS Registry No.: 4697-36-3); Mezlocillin (CAS Registry No.: 51481-65-3); Azlocillin (CAS Registry No.: 37091-66-0); Piperacillin (CAS Registry No.: 61477-96-1); Imipenem (CAS Registry No.: 74431-23-5); Aztreonam (CAS Registry No.: 78110-38-0); Cephalothin (CAS Registry No.: 153-61-7); Cefazolin (CAS Registry No.: 25953-19-9); Cefaclor (CAS Registry No.: 70356-03-5); Cefamandole formate sodium (CAS Registry No.: 42540-40-9); Cefoxitin (CAS Registry No.: 35607-66-0); Cefuroxime (CAS Registry No.: 55268-75-2); Cefonicid (CAS Registry No.: 61270-58-4); Cefmetazole (CAS Registry No.: 56796-20-4); Cefotetan (CAS Registry No.: 69712-56-7); Cefprozil (CAS Registry No.: 92665-29-7); Loracarbef (CAS Registry No.: 121961-22-6); Cefetamet (CAS Registry No.: 65052-63-3); Cefoperazone (CAS Registry No.: 62893-19-0); Cefotaxime (CAS Registry No.: 63527-52-6); Ceftizoxime (CAS Registry No.: 68401-81-0); Ceftriaxone (CAS Registry No.: 73384-59-5); Ceftazidime (CAS Registry No.: 72558-82-8); Cefepime (CAS Registry No.: 88040-23-7); Cefixime (CAS Registry No.: 79350-37-1); Cefpodoxime (CAS Registry No.: 80210-62-4); Cefsulodin (CAS Registry No.: 62587-73-9); Fleroxacin (CAS Registry No.: 79660-72-3); Nalidixic acid (CAS Registry No.: 389-08-2); Norfloxacin (CAS Registry No.: 70458-96-7); Ciprofloxacin (CAS Registry No.: 85721-33-1); Ofloxacin (CAS Registry No.: 82419-36-1); Enoxacin (CAS Registry No.: 74011-58-8); Lomefloxacin (CAS Registry No.: 98079-51-7); Cinoxacin (CAS Registry No.: 28657-80-9); Doxycycline (CAS Registry No.: 564-25-0); Minocycline (CAS Registry No.: 10118-90-8); Tetracycline (CAS Registry No.: 60-54-8); Amikacin (CAS Registry No.: 37517-28-5); Gentamicin (CAS Registry No.: 1403-66-3); Kanamycin (CAS Registry No.: 8063-07-8); Netilmicin (CAS Registry No.: 56391-56-1); Tobramycin (CAS Registry No.: 32986-56-4); Streptomycin (CAS Registry No.: 57-92-1); Azithromycin (CAS Registry No.: 83905-01-5); Clarithromycin (CAS Registry No.: 81103-11-9); Erythromycin (CAS Registry No.: 114-07-8); Erythromycin estolate (CAS Registry No.: 3521-62-8); Erythromycin ethyl succinate (CAS Registry No.: 41342-53-4); Erythromycin glucoheptonate (CAS Registry No.: 23067-13-2); Erythromycin lactobionate (CAS Registry No.: 3847-29-8); Erythromycin stearate (CAS Registry No.: 643-22-1); Vancomycin (CAS Registry No.: 1404-90-6); Teicoplanin (CAS Registry No.: 61036-64-4); Chloramphenicol (CAS Registry No.: 56-75-7); Clindamycin (CAS Registry No.: 18323-44-9); Trimethoprim (CAS Registry No.: 738-70-5); Sulfamethoxazole (CAS Registry No.: 723-46-6); Nitrofurantoin (CAS Registry No.: 67-20-9); Rifampin (CAS Registry No.: 13292-46-1); Mupirocin (CAS Registry No.: 12650-69-0); Metronidazole (CAS Registry No.: 443-48-1); Cephalexin (CAS Registry No.: 15686-71-2); Roxithromycin (CAS Registry No.: 80214-83-1); Co-amoxiclavuanate; combinations of Piperacillin and Tazobactam; and their various salts, acids, bases, and other derivatives.

Anti-fingal agents include but are not limited to Amphotericin B, Candicidin, Dermostatin, Filipin, Fungichromin, Hachimycin, Hamycin, Lucensomycin, Mepartricin, Natamycin, Nystatin, Pecilocin, Perimycin, Azaserine, Griseofulvin, Oligomycins, Neomycin, Pyrrolnitrin, Siccanin, Tubercidin, Viridin, Butenafine, Naftifine, Terbinafine, Bifonazole, Butoconazole, Chlordantoin, Chlormidazole, Cloconazole, Clotrimazole, Econazole, Enilconazole, Fenticonazole, Flutrimazole, Isoconazole, Ketoconazole, Lanoconazole, Miconazole, Omoconazole, Oxiconazole, Sertaconazole, Sulconazole, Tioconazole, Tolciclate, Tolindate, Tolnaftate, Fluconawle, Itraconazole, Saperconazole, Terconazole, Acrisorcin, Amorolfine, Biphenamine, Bromosalicylchloranilide, Buclosamide, Calcium Propionate, Chlorphenesin, Ciclopirox, Cloxyquin, Coparaffinate, Diamthazole, Exalamide, Flucytosine, Halethazole, Hexetidine, Loflucarban, Nifuratel, Potassium Iodide, Propionic Acid, Pyrithione, Salicylanilide, Sodium Propionate, Sulbentine, Tenonitrozole, Triacetin, Ujothion, Undecylenic Acid, and Zinc Propionate.

Antiviral agents include, but are not limited to, Acyclovir, Cidofovir, Cytarabine, Dideoxyadenosine, Didanosine, Edoxudine, Famciclovir, Floxuridine, Ganciclovir, Idoxuridine, Inosine Pranobex, Lamivudine, MADU, Penciclovir, Sorivudine, Stavudine, Trifluridine, Valacyclovir, Vidarabine, Zalcitabine, Zidovudine, Acemannan, Acetylleucine, Amantadine, Amidinomycin, Delavirdine, Foscamet, Indinavir, Interferon-alpha, Interferon-beta, Interferon-gamma, Kethoxal, Lysozyme, Methisazone, Moroxydine, Nevirapine, Podophyllotoxin, Ribavirin, Rimantadine, Ritonavir2, Saquinavir, Stailimycin, Statolon, Tromantadine, and Xenazoic Acid.

Antiinflammatory agents include, but are not limited to, Enfenamic Acid, Etofenamate, Flufenamic Acid, Isonixin, Meclofenamic Acid, Mefenamic Acid, Niflumic Acid, Talniflumate, Terofenamate, Tolfenamic Acid, Aceclofenac, Acemetacin, Alclofenac, Amfenac, Amtolmetin Guacil, Bromfenac, Bufexamac, Cinmetacin, Clopirac, Diclofenac, Etodolac, Felbinac, Fenclozic Acid, Fentiazac, Glucametacin, Ibufenac, Indomethacin, Isofezolac, Isoxepac, Lonazolac, Metiazinic Acid, Mofezolac, Oxametacine, Pirazolac, Proglumetacin, Sulindac, Tiaramide, Tolmetin, Tropesin, Zomepirac, Bumadizon, Butibufen, Fenbufen, Xenbucin, Clidanac, Ketorolac, Tinoridine, Alminoprofen, Benoxaprofen, Bermoprofen, Bucloxic Acid, Carprofen, Fenoprofen, Flunoxaprofen, Flurbiprofen, Ibuprofen, Ibuproxam, Indoprofen, Ketoprofen, Loxoprofen, Naproxen, Oxaprozin, Piketoprofen, Pirprofen, Pranoprofen, Protizinic Acid, Suprofen, Tiaprofenic Acid, Ximoprofen, Zaltoprofen, Difenamizole, Epirizole, Apazone, Benzpiperylon, Feprazone, Mofebutazone, Morazone, Oxyphenbutazone, Phenylbutazone, Pipebuzone, Propyphenazone, Ramifenazone, Suxibuzone, Thiazolinobutazone, Acetaminosalol, Aspirin, Benorylate, Bromosaligenin, Calcium Acetylsalicylate, Diflunisal, Etersalate, Fendosal, Gentisic Acid, Glycol Salicylate, Imidazole Salicylate, Lysine Acetylsalicylate, Mesalamine, Morpholine Salicylate, I-Naphthyl Salicylate, Olsalazine, Parsalmide, Phenyl Acetylsalicylate, Phenyl Salicylate, Salacetamide, Salicylamide O-Acetic Acid, Salicylsulfuric Acid, Salsalate, Sulfasalazine, Ampiroxicam, Droxicam, Isoxicam, Lomoxicam, Piroxicam, Tenoxicam, epsilon-Acetamidocaproic Acid, S-Adenosylmethionine, 3-Amino-4-hydroxybutyric Acid, Amixetrine, Bendazac, Benzydamine, alpha-Bisabolol, Bucolome, Difenpiramide, Ditazol, Emorfazone, Fepradinol, Guaiazulene, Nabumetone, Nimesulide, Oxaceprol, Paranyline, Perisoxal, Proquazone, Superoxide Dismutase, Tenidap, Zileuton, 21-Acetoxypregnenolone, Alclometasone, Algestone, Amcinonide, Beclomethasone, Betamethasone, Budesonide, Chloroprednisone, Clobetasol, Clobetasone, Clocortolone, Cloprednol, Corticosterone, Cortisone, Cortivazol, Deflazacort, Desonide, Desoximetasone, Dexamethasone, Diflorasone, Diflucortolone, Difluprednate, Enoxolone, Fluazacort, Flucloronide, Flumethasone, Flunisolide, Fluocinolone Acetonide, Fluocinonide, Fluocortin Butyl, Fluocortolone, Fluorometholone, Fluperolone Acetate, Fluprednidene Acetate, Fluprednisolone, Flurandrenolide, Fluticasone Propionate, Formocortal, Halcinonide, Halobetasol Propionate, Halometasone, Halopredone Acetale, Hydrocortamate, Hydrocortisone, Loteprednol Etabonale, Mazipredone, Medrysone, Meprednisone, Methylprednisolone, Mometasone Furoate, Paramethasone, Prednicarbate, Prednisolone, Prednisolone 25-Diethylaminoacetate, Prednisolone Sodium Phosphate, Prednisone, Prednival, Prednylidene, Rimexolone, Tixocortol, Triamcinolone, Triamcinolone Acetonide, Triamcinolone Benetonide, and Triamcinolone Hexacetonide.

Compounds of the invention may be combined with one or more Beta lactamase inhibitor when used in combination with a beta-lactam class antibiotic, such as penicillin or cephalosporins. Beta-lactamase inhibitors include, but are not limited to Clavulanic acid, Sulbactam, Sultamacillin, and Tazobactam.

Compounds of the invention may also be combined with one or more efflux pump inhibitor, such as a quinazolinone efflux pump inhibitors, d-ornithine-d-homophenylalanine-3-aminoquinoline, Phe-Arg-b-naphthylamide, propafenone, a phenothiazine or thioxanthene efflux pump inhibitor, 1-aza-9-oxafluorenes, N-[4-[2-(3,4-dihydro-6,7-dimethoxy-2(1H)-isoquinolinyl)ethyl]phenyl]-9,10-dihydro-5-methoxy-9-oxo-4-Acridinecarboxamide, reserpine, Milbemycin, Cinchonine, Verapamil, L-phenylalanyl-N-2-naphthalenyl-L-Argininamide (and analogs), 5'-methoxyhydnocarpin-D, methylxanthines, FK506, a cyclosporine efflux pump inhibitor, Nocardamine and other siderophores, Amiodarone, Cyclosporin A, Ro11-2933 (DMDP), Quinidine, and the optical isomers of Propranolol, Quinine (SQ1) and Quinidine, Quinine-10,11-epoxide, Quercetin, Amitriptyline, Taxuspine C derivatives, Emodin, MC-002434; Agosterol A; Pheophorbide; pyridoquinolines such as 2,2'-[(2,8,10-trimethylpyrido[3,2-g]quinoline-4,6-diyl)bis(oxy)]bis[N,N-dimethyl-ethanamine, Gitonavir, and Gemfibrozil.

Synthesis of Compounds

The starting materials used in preparing the compounds of the invention are known, made by known methods, or are commercially available.

It is recognized that the skilled artisan in the art of organic chemistry can readily carry out standard manipulations of organic compounds without further direction. Examples of such manipulations are discussed in standard texts such as J. March, Advanced Organic Chemistry, John Wiley & Sons, 1992. Those skilled in the art of organic synthesis will recognize that reactions conditions and starting materials will vary on occasion from those set forth in the synthetic examples included herein depending of the desired final product.

The skilled artisan will readily appreciate that certain reactions are best carried out when other functionalities are masked or protected in the compound, thus increasing the yield of the reaction and/or avoiding any undesirable side reactions. Often, the skilled artisan utilizes protecting groups to accomplish such increased yields or to avoid the undesired reactions. These reactions are found in the literature and are also well within the scope of the skilled artisan. Examples of many such manipulations can be found in, for example, T. Greene, *Protecting Groups in Organic Synthesis*, John Wiley & Sons, 1981.

The compounds of the invention may have one or more chiral center. As a result, one may selectively prepare one optical isomer, including diastereomers and enantiomers, over another, for example by chiral starting materials, catalysts or solvents, or may prepare both stereoisomers or both optical isomers, including diastereomers and enantiomers at once (a racemic mixture). Since the compounds of the invention may exist as racemic mixtures, mixtures of optical isomers, including diastereomers and enantiomers, or stereoisomers may be separated using known methods, such as through the use of, for example, chiral salts and chiral chromatography.

In addition, it is recognized that one optical isomer, including a diastereomer and enantiomer, or a stereoisomer, may have favorable properties over the other. When a racemic mixture is discussed herein, it is clearly contemplated to include both optical isomers, including diastereomers and enantiomers, or one stereoisomer substantially free of the other.

The invention also includes also includes all energetically accessible conformational and torsional isomers of the compounds disclosed.

When the substituent $R_7$ in a compound of Formula I or Formula II is attached via an unsaturated aliphatic group, for example when $R_7$ is (phenyl)$C_2C6$alkenyl, all geometric isomers of the compound are included. This invention is further illustrated by the following examples that should not be construed as limiting. The contents of all references, patents and published patent applications cited throughout this application are incorporated herein by reference.

EXAMPLES

Abbreviations

The following abbreviations are used in the reaction schemes and synthetic examples, which follow. This list in not meant to be an all-inclusive list of abbreviations used in the application as additional standard abbreviations, which are readily understood by those skilled in the art of organic synthesis, may also be used in the synthetic schemes and examples:

DMF—N,N-Dimethylformamide
DMSO—Dimethylsulfoxide
LDA—Lithium diisopropylamide
Pd(PPh$_3$)$_4$-Tetrakis(triphenylphosphine)palladium(0)
TFA Trifluoroacetic acid General Methods All nonaqueous reactions are performed under an atmosphere of dry argon gas (99.99%) using oven- or flame-dried glassware. All isolated products are stored for prolonged periods under an atmosphere of argon at −20° C. Microwave-assisted syntheses are conducted in a commercial microwave reactor (Discover System, CEM Corporation). The progress of reactions is monitored using thin-layer chromatography on glass plates coated with Merck silica gel 60 (F254). Flash column chromatography is performed on Merck silica gel 60 (230-400 mesh). Melting points are recorded on an Electrothermal Model IA9100 digital melting point apparatus. NMR spectra are recorded at ambient temperature using a Bruker Avance 300 spectrometer ($^1$H at 300.1 MHz, $^{13}$C at 75.5 MHz, and $^{15}$N at 30.4 MHz). The chemical shifts for $^1$H and $^{13}$C are reported in parts per million (δ) relative to external tetramethylsilane and are referenced to signals of residual protons in the deuterated solvent. The chemical shifts for $^{15}$N are reported in parts per million (δ) relative to external liquid ammonia. Assignment of 1H and $^{13}$C NMR data is based on extensive two-dimensional correlation experiments ($^1$H—$^1$H COSY, $^1$H—$^{13}$C HMQC, $^1$H—$^{13}$C HMBC, and $^1$H—$^1$H NOESY spectra recorded using standard pulse sequences) and the usual principles of NMR spectroscopy (the magnitudes of coupling constants and chemical shifts). Analytical HPLC is performed using a YMC Pack Pro C18 50×4.6 mm 5 μm column with an isocratic elution of 0.24 min at 95:5 H$_2$O:CH$_3$CN containing 0.1% TFA followed by a 20-min linear gradient elution from 95:5 to 5:95 at a flow rate of 1.0 mL/min with UV detection at 254 nm. Low-resolution mass spectra are recorded on a Thermo Finnigan Surveyor MSQ instrument (operating in API mode) equipped with a Gilson liquid chromatograph. High-resolution mass spectrometric analyses (ESI using sodium iodide as internal standard) are performed at the W. M. Keck Foundation Biotechnology Resource Laboratory (Yale University, New Haven, Conn.). Elemental analyses are performed at Atlantic Microlab, Inc. (Norcross, Ga.) and Prevalere Life Sciences, Inc. (Whitesboro, N.Y.).

Example 1

Preparation of 10-ethyl-8-phenyl-2H-isothiazolo[5,4-b]quinolizine-3,4-dione (7)

After the addition of diethyl malonate is complete, the gray reaction mixture continues to stir at 0° C. for 15 min. Carbon disulfide (14.5 mL, 0.24 mol) is then added dropwise to give a red mixture that is allowed to warm to room temperature with stirring for 1 h. A solution of dimethylformamide (25 mL) containing 4-methoxybenzyl chloride (25.00 g, 0.16 mol) is added dropwise to the reaction mixture at room temperature. The resulting orange mixture is allowed to warm to room temperature with stirring for 15 h, diluted with water (500 mL), and extracted with ethyl acetate (4×500 mL). The combined extracts are concentrated under reduced pressure (~1 L), washed with water (3×150 mL), washed with brine (3×150 mL), dried over magnesium sulfate, and evaporated under reduced pressure to give crude 1. The crude product is purified by flash column chromatography (eluting with ethyl

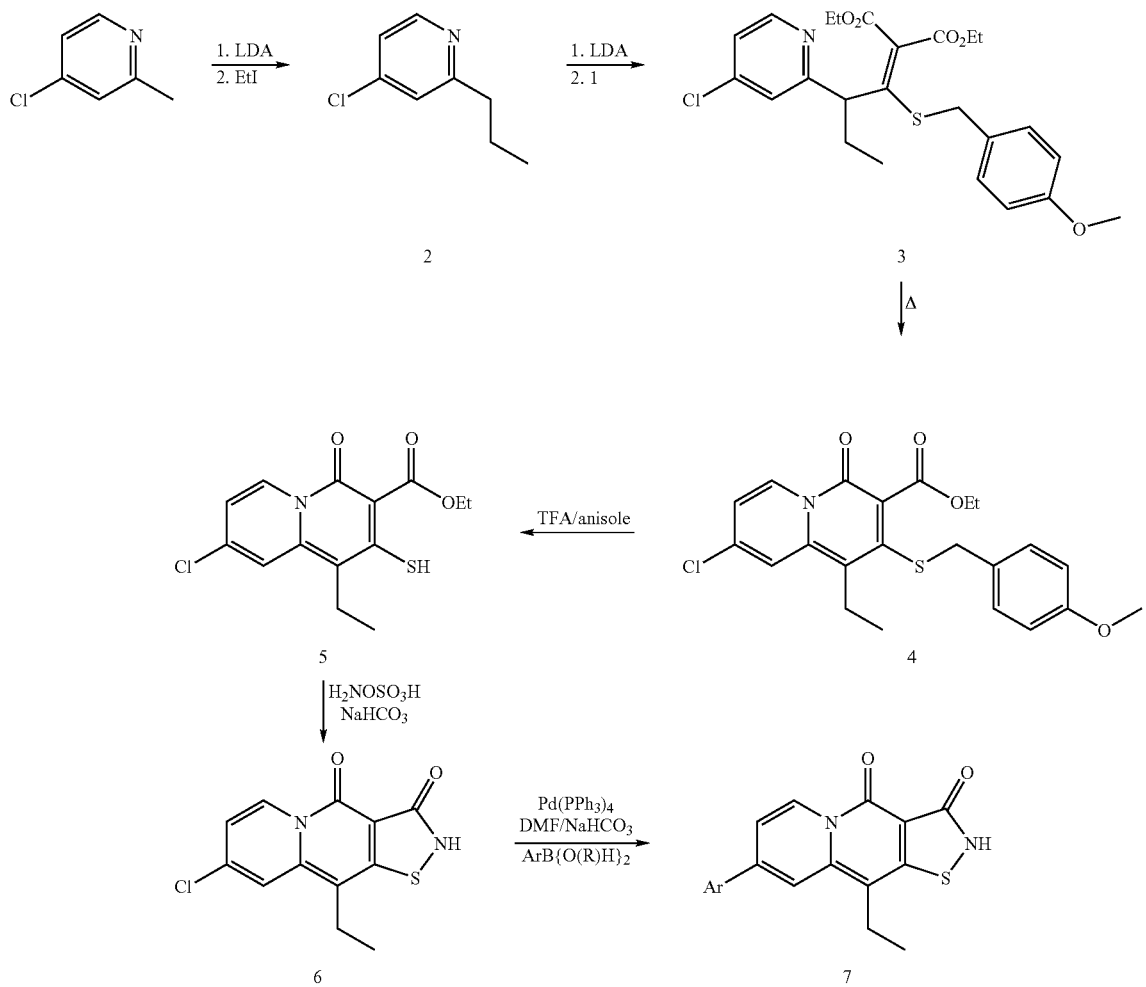

Step 1. Diethyl 2-[bis(4-methoxybenzylsulfanyl)methylene]malonate (1)

A solution of dimethylformamide (50 mL) containing diethyl malonate (12.78 g, 0.08 mol) is added slowly to an ice-cooled suspension of sodium hydride (60% dispersion in mineral oil, 6.53 g, 0.16 mol) in dimethylformamide (500 mL). The rate of addition of diethyl malonate is such as to maintain the temperature of the reaction mixture below 5° C.

acetate/hexanes=1:4; Rf 0.21) to give 1 as a yellow solid. mp 57-59° C. $^1$H NMR (CDCl3): δ 1.27 (t, J=7.0 Hz, 3H, $CO_2CH_2CH_3$), 3.79 (s, 3H, $OCH_3$), 4.07 (s, 2H, $SCH_2$), 4.23 (q, J=7.0 Hz, 2H, $CO_2CH_2CH_3$), 6.83 (m, 2H, H-3/H-5), 7.20 (m, 2H, H-2/H-6). $^{13}C\{^1H\}$ NMR (CDCl$_3$): δ 14.0 ($CO_2CH_2CH_3$), 40.3 ($SCH_2$), 55.3 ($OCH_3$), 61.4 ($CO_2CH_2CH_3$), 114.1 (aromatic C-3/C-5), 128.1 (=C—$CO_2CH_2CH_3$ or C—$CH_2S$—), 128.7 (=C—$CO_2CH_2CH_3$ or C—CH$_2$S—), 130.4 (aromatic C-2/C-6), 155.6 (—CH$_2$S—C=), 159.1 (aromatic C-4, C—OCH$_3$), 163.9 (CO$_2$CH$_2$CH$_3$). LCMS m/z calcd for C$_{24}$H$_{28}$O$_6$S$_2$ 476 ([M+]). found 477 ([M+H]+). HRMS m/z calcd for C$_{24}$H$_{28}$NaO$_6$S$_2$ 499.1225 ([M+Na]+). found 499.1230. Anal. Calcd for C$_{24}$H$_{28}$O$_6$S$_2$: C, 60.48; H, 5.92; S, 13.46. Found: C, 60.51; H, 5.97; S, 13.19.

Step 2. 4-Bromo-2-propylpyridine (2)

Prepared by a method analogous to the preparation of 5-Chloro-2-propylpyridine, described previously (Li, Q., et al. J. Med. Chem. 39: 3070-3088 (1996)). The crude product is purified by flash column chromatography (eluting with ethyl acetate/hexanes=1:2; Rf 0.56) to give 2 as an amber liquid.

$^1$H NMR (CDCl$_3$): δ 0.97 (t, J=7.5 Hz, 3H, CH$_2$CH$_2$CH$_3$), 1.74 (m, 2H, CH$_2$CH$_2$CH$_3$), 2.75 (m, 2H, CH$_2$CH$_2$CH$_3$), 7.11 (dd, J=5.5 Hz, 1.5 Hz, 1H, pyridyl H-5), 7.16 (d, J=1.5 Hz, 1H, pyridyl H-3), 8.42 (d, J=5.5 Hz, 1H, pyridyl H-6). $^{13}$C{$^1$H} NMR (CDCl$_3$): δ 13.8 (CH$_2$CH$_2$CH$_3$), 22.8 (CH$_2$CH$_2$CH$_3$), 40.1 (CH$_2$CH$_2$CH$_3$), 121.3 (CH, C-5), 123.0 (CH, C-3), 144.1 (C-4, C-Cl), 150.1 (CH, C-6), 164.0 (C-2). LCMS m/z calcd for C$_8$H$_{10}$ClN 155 ([M+]). found 156 ([M+H]+). HRMS m/z calcd for C8H$_{11}$ClN 156.0580 ([M+H]+). found 156.0578.

Step 3. (E)-diethyl 2-(1-(4-methoxybenzylthio)-2-(4-bromopyridin-2-yl)but-1-enyl)malonate (3)

Lithium diisopropylamide (LDA) is formed by dropwise addition of n-butyllithium (1.6 M in hexanes, 10.1 mL, 16.2 mmol) to a stirred solution of diisopropylamine (2.3 mL, 16.4 mmol) in tetrahydrofuran (25.0 mL) at −78° C. The resulting solution is stirred at −78° C. for 5 min, 0° C. for 15 min, and then recooled to −78° C. A solution of 4-bromo-2-propylpyridine (2, 2.94 g, 14.7 mmol) in tetrahydrofuran (25.0 mL) is added dropwise to this solution over a period of 30 min. The resulting deep red suspension is stirred at −78° C. for 1 h, after which time a solution of diethyl 2-[bis(4-methoxybenzylsulfanyl)methylene]malonate (1, 7.03 g, 14.8 mmol) in tetrahydrofuran (40.0 mL) is added dropwise over a period of 15 min. The resulting yellow solution is stirred at −78° C. for 1.5 h, −15° C. for 1.5 h, and room temperature for 30 min to give a dark orange solution. The reaction mixture is quenched with a saturated aqueous solution of ammonium chloride (100 mL) and extracted with diethyl ether (2×100 mL). The combined organic extracts are dried over magnesium sulfate and evaporated under reduced pressure to give 3 an orange oil. The product is purified by flash column chromatography (eluting with 5% ethyl acetate in methylene chloride.

$^1$H NMR (DMSO-d6): δ 0.76 (t, J=7.5 Hz, 3H, CH$_2$CH$_3$), 1.17 (t, J=7.0 Hz, 6H, 2×CO$_2$CH$_2$CH$_3$), 2.81 (q, J=7.5 Hz, 2H, CH$_2$CH$_3$), 3.74 (s, 3H, OCH$_3$), 4.01 (s, 2H, SCH$_2$), 4.10 (q, J=7.0 Hz, 4H, 2×CO$_2$CH$_2$CH$_3$), 4.41 (s, 1H, CH(CO$_2$CH$_2$CH$_3$)$_2$), 6.90 (m, 2H, benzylic H-3/H-5), 7.28 (m, 2H, benzylic H-2/H-6), 7.44 (d, J=2.0 Hz, 1H, pyridyl H-3), 7.52 (dd, J=5.5 Hz, 2.0 Hz, 1H, pyridyl H-5), 8.56 (d, J=5.5 Hz, 1H, pyridyl H-6). $^{13}$C{$^1$H} NMR (DMSO-d6): δ 12.4 (CH$_2$CH$_3$), 13.9 (CH(CO$_2$CH$_2$CH$_3$)$_2$), 28.3 (CH$_2$CH$_3$), 39.5 (SCH$_2$), 55.0 (OCH$_3$), 58.5 (CH(CO$_2$CH$_2$CH$_3$)$_2$), 61.1 (CH(CO$_2$CH$_2$CH$_3$)$_2$), 113.9 (benzylic C-3/C-5), 122.9 (pyridyl C-5), 123.0 (pyridyl C-3), 125.7 (=C(SAr)(CH(CO$_2$CH$_2$CH$_3$)$_2$)), 129.3 (benzylic C-1), 130.2 (benzylic C-2/C-6), 143.4 (pyridyl C-4, C—Cl), 150.6 (pyridyl C-6), 153.3 (=C(CH$_2$CH$_3$)(pyridyl)), 158.4 (benzylic C-4, C—OCH$_3$), 159.1 (pyridyl C-1), 167.2 (CH(CO$_2$CH$_2$CH$_3$)$_2$). LCMS m/z calcd for C$_{24}$H$_{28}$ClNO$_5$S 477 ([M+]). found 478 ([M+H]+).

Step 4. Ethyl 8-chloro-1-ethyl-2-(4-methoxybenzylsulfanyl)-4-oxo-4H-quinolizine-3-carboxylate (4)

A solution of 3 (1.93 g, 4.04 mmol) in dimethyl sulfoxide (10.0 mL) is heated at 120° C. for 5.5 h, cooled to room temperature, and concentrated under reduced pressure to give a yellowish brown oil that solidifies upon standing. The crude product is purified by flash column chromatography (eluting with 20% ethyl acetate in methylene chloride; Rf 0.53) to give pure 4 as a bright yellow solid. Because 4 oxidizes slowly in solution under ambient conditions, the purified material is stored for prolonged periods as a solid under an atmosphere of argon in the absence of light.

mp 159-160° C. $^1$H NMR (CDCl$_3$): δ 1.09 (t, J=7.5 Hz, 3H, CH$_2$CH$_3$), 1.44 (t, J=7.0 Hz, 3H, CO$_2$CH$_2$CH$_3$), 2.87 (q, J=7.5 Hz, 2H, CH$_2$CH$_3$), 3.77 (s, 3H, OCH$_3$), 4.10 (s, 2H, SCH$_2$), 4.51 (q, J=7.0 Hz, 2H, CO$_2$CH$_2$CH$_3$), 6.78 (m, 2H, benzylic H-3/H-5), 7.01 (dd, J=8.0 Hz, 2.0 Hz, 1H, pyridone H-7), 7.16 (m, 2H, benzylic H-2/H-6), 7.63 (d, J=2.0 Hz, 1H, pyridone H-9), 9.16 (d, J=8.0 Hz, 1H, pyridone H-6). $^{13}$C{$^1$H} NMR (CDCl$_3$): δ 14.2 (CO$_2$CH$_2$CH$_3$), 14.9 (CH$_2$CH$_3$), 22.0 (CH$_2$CH$_3$), 41.6 (SCH$_2$), 55.3 (OCH$_3$), 62.0 (CO$_2$CH$_2$CH$_3$), 113.9 (benzylic C-3/C-5), 116.9 (C-7, CH), 119.1 (C-1), 121.0 (C-3), 121.1 (C-9, CH), 128.8 (benzylic C-1), 130.0 (C-6, CH), 130.2 (benzylic C-2/C-6), 138.3 (C-8, C—Cl), 139.2 (C-9a), 144.5 (C-2, C—SCH$_2$), 154.0 (C-4, NC(O)), 159.1 (benzylic C-4), 166.5 (CO$_2$CH$_2$CH$_3$). LCMS m/z calcd for C$_{22}$H$_{22}$ClNO$_4$S 431 ([M+]). found 432 ([M+H]+). HRMS m/z calcd for C$_{22}$H$_{22}$ClNNaO$_4$S 454.0856 ([M+Na]+). found 454.0853. Anal. Calcd for C$_{22}$H$_{22}$ClNO$_4$S: C, 61.18; H, 5.13; N, 3.24. Found: C, 61.33; H, 5.15; N, 3.33.

Step 5. Ethyl 8-bromo-1-ethyl-2-mercapto-4-oxo-4H-quinolizine-3-carboxylate (5)

A solution containing 4 (1.0306 g, 2.39 mmol), trifluoroacetic acid (100 g), and anhydrous anisole (20.0 mL) is heated at 40° C. for 23 h. The resulting amber solution is evaporated under reduced pressure (~1 mm Hg, 40° C.) to give an oily residue containing ethyl 8-bromo-1-ethyl-2-mercapto-4-oxo-4H-quinolizine-3-carboxylate (5) that is used directly in the next step of the synthesis.

$^1$H NMR (CDCl$_3$): δ 1.22 (br, 3H, CH$_2$CH$_3$), 1.44 (t, J=7.0 Hz, 3H, CO$_2$CH$_2$CH$_3$), 2.88 (br, 2H, CH$_2$CH$_3$), 4.48 (br, 2H, CO$_2$CH$_2$CH$_3$), 5.85 (br, 1H, SH), 6.92 (dd, J=8.0 Hz, 2.0 Hz, 1H, H-7), 7.53 (br, 1H, H-9), 9.12 (d, J=8.0 Hz, 1H, H-6). LCMS m/z calcd for C$_{14}$H$_{14}$ClNO$_3$S 311 ([M+]). found 312 ([M+H]+).

Step 6. 7-Chloro-9-ethyl-1-thia-2,4a-diazacyclopenta[b]naphthalene-3,4-dione (6)

A solution of sodium bicarbonate (2.00 g, 23.8 mmol) in water (60 mL) is added to a solution of 5 (from above, ~2.39 mmol) in tetrahydrofuran (60 mL) at room temperature. Hydroxylamine-O-sulfonic acid (1.08 g, 9.55 mmol) is added to this mixture as a solid and in one portion. The resulting yellow mixture is stirred at room temperature for 3.5 h and quenched by addition of an aqueous solution of 5% hydrochloric acid (500 mL). The precipitate that forms is collected by filtration, washed with distilled water (3×50 mL), washed exhaustively with diethyl ether, and dried in vacuo to give pure 6 as a yellow solid. Because 6 decomposes slowly in solution under ambient conditions, the purified material is stored for prolonged periods as a solid under an atmosphere of argon in the absence of light.

Rf 0.25 (methylene chloride/methanol/acetic acid≈200/10/1). mp 222-223° C. $^1$H NMR (DMSO-d6): δ 1.14 (t, J=7.5 Hz, 3H, CH$_2$CH$_3$), 2.75 (q, J=7.5 Hz, 2H, CH$_2$CH$_3$), 7.05 (dd, J=8.0 Hz, J=2.0 Hz, 1H, pyridone H-6), 7.87 (d, J=2.0 Hz, 1H, pyridone H-8), 8.89 (d, J=8.0 Hz, 1H, pyridone H-5). $^{13}$C{$^1$H} NMR (DMSO-d6): δ 13.3 (CH$_2$CH$_3$), 21.6 (CH$_2$CH$_3$), 104.0 (br, C-3a), 106.1 (C-9), 114.4 (C-6, CH), 119.3 (C-8, CH), 129.7 (C-5, CH), 137.2 (C-7, C—Cl), 137.5 (C-8a), 152.9 (C-4, NC(O)), 160.9 (br, C-9a, C—S), 166.8 (C-3, CONS). LCMS m/z calcd for C$_{12}$H$_9$ClN$_2$O$_2$S 280 ([M+]). found 281 ([M+H]+). HRMS m/z calcd for C$_{12}$H$_9$ClN$_2$NaO$_2$S 302.9971 ([M+Na]+). found 302.9969. Anal. Calc'd for C$_{12}$H$_9$ClN$_2$O$_2$S.H$_2$O: C, 48.24; H, 3.71; N, 9.38. Found: C, 48.06; H, 3.40; N, 9.16.

Step 6a. [2-$^{15}$N]-7-Chloro-9-ethyl-1-thia-2,4a-diaza-cyclopenta[b]naphthalene-3,4-dione ([2-$^{15}$N]-7)

This compound is prepared as outlined above for 6 using [$^{15}$N]hydroxylamine-O-sulfonic acid (98+ atom %). The $^{13}$C NMR spectrum of [2-$^{15}$N]-6 is identical to that reported above for 6 with one exception that follows. $^{13}$C{$^1$H} (DMSO-d6): δ 166.8 (d, 1JN—C=3.5 Hz). Because exchange of the N—H group of [2-$^{15}$N]-6 is rapid (the corresponding broad 1H resonance showed rapid H-D exchange with D$_2$O at room temperature), it is necessary to cool samples to obtain $^{15}$N NMR spectroscopic data. $^{15}$N NMR (DMF-d7, −50° C.): δ 104.6 (s). In accord with the $^{15}$N data recorded at low temperature, no 1JN-H coupling was observed in 1H NMR spectra of [2-$^{15}$N]-7 recorded in DMF-d7 at temperatures ranging from +60 to −55° C. LCMS m/z calcd for C$_{12}$H$_9$ClN$_{15}$NO$_2$S ([M]+) 281. found 282 ([M+H]+).

Step 7. 10-ethyl-8-phenyl-2H-isothiazolo[5,4-b]quinolizine-3,4-dione (7)

Pd(PPh$_3$)$_4$ (3.1 mg, 6% mole), boronic acid or ester (2 equiv., 0.088 mmole) and NaHCO$_3$ solution (1M, 0.2 mL, 4.5 equiv.) under argon at room temperature is added to a stirred solution of 7-Bromo-9-ethyl-1-thia-2,4a-diazacyclopenta[b]naphthalene-3,4-dione 0.044 mmole) in DMF (1 mL). The reaction mixture is degassed by bubbling argon through for 10 minutes at room temperature. The reaction tube is sealed and then heated in a microwave (100 W, 130° C.) until the reaction reaches completion (10-20 minutes). The reaction mixture is cooled to room temperature and then filtered. The filtrate is concentrated in vacuo. The residue is dissolved in a mixture of DMF:CHCl$_3$:MeOH (0.5:3:0.5) (4 mL) and precipitated with diethyl ether. This dissolution and precipitation step is repeated 5 times. The resulting light yellow solid is washed with water (3 mL) and dried to afford the title compound.

General information concerning the preparation of C—C bond at C-7 of a pyridone core via Suzuki cross-coupling may be found in Otten, P. A. et al,. Bioconjugate Chem. (2001) 12: 203-212.

Example 2

Preparative HPLC Conditions

Preparative HPLC was performed using a YMC Pack Pro C18 150×20.0 mm 5 μm column with an isocratic elution of 0.35 min at 90:10 water:acetonitrile containing 0.1% trifluoroacetic acid followed by a 23.6-min linear gradient elution from 90:10 to 10:90 at a flow rate of 18.9 mL/min with UV detection at 254 nm. Analytical HPLC was performed using a YMC Pack Pro C18 50×4.6 mm 5 μm column with an isocratic elution of 0.24 min at 95:5 water:acetonitrile containing 0.1% trifluoroacetic acid followed by a 20-min linear gradient elution from 95:5 to 5:95 at a flow rate of 1.0 mL/min with UV detection at 254 nm.

Example 3

9-Ethyl-7-pyridin-4-yl-1-thia-2,4a-diaza-cyclopenta[b]naphthalene-3,4-dione hydrochloride (8)

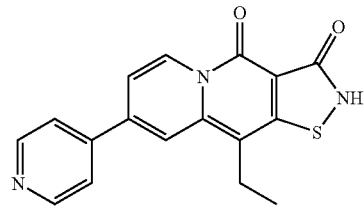

Tetrakis(triphenylphosphine)palladium(0) (26.1 mg, 0.023 mmol), 4-pyridinylboronic acid (89.4 mg, 0.727 mmol), and a 1 M aqueous solution of sodium bicarbonate (2.2 mL, 2.2 mmol) are added sequentially under an atmosphere of argon, to a solution containing 7-chloro-9-ethyl-1-thia-2,4a-diazacyclopenta[b]naphthalene-3,4-dione (40.9 mg, 0.145 mmol) and dimethylformamide (4.0 mL). The resulting orange mixture is irradiated in a microwave for 15 min (110° C.; 300 W) to give a red mixture. The solvent is evaporated under reduced pressure (~10 mm Hg, 50° C.), and the remaining solid washed with diethyl ether (3×15 mL). The product is extracted from this solid using hot dimethyl sulfoxide (5×2 mL) and purified by preparative HPLC. The purified product is isolated as the trifluoroacetate salt and converted to the hydrochloride salt by addition of a solution of hydrogen chloride (~1.25 M in methanol) followed by evaporation to give a deep red solid; this process is repeated twice.

Purity by HPLC: 98.3%; tR=4.98 min. mp 289-290° C. dec. $^1$H NMR (DMSO-d6): δ 1.22 (t, J=7.5 Hz, 3H, CH$_2$CH$_3$), 2.97 (q, J=7.5 Hz, 2H, CH$_2$CH$_3$), 7.52 (dd, J=8.0 Hz, J=1.5 Hz, 1H, pyridone H-6), 8.25 (d, J=1.5 Hz, 1H, pyridone H-8), 8.40 (d, J=6.0 Hz, AA' part of AA'XX' spin system, 2H, pyridinyl H-3/H-5), 8.96 (d, J=6.0 Hz, XX' part of AA'XX' spin system, 2H, pyridinyl H-2/H-6), 9.02 (d, J=8.0 Hz, 1H, pyridone H-5). $^{13}$C{1H} NMR (DMSO-d6): δ 13.7 (CH$_2$CH$_3$), 21.8 (CH$_2$CH$_3$), 105.3 (C-3a), 109.5 (C-9), 110.8 (C-6, CH), 121.4 (C-8, CH), 123.9 (pyridinyl C-3/C-5), 128.8 (C-5, CH), 136.5 (C-7), 136.7 (C-8a), 143.7 (pyridinyl C-2/C-6), 149.9 (pyridinyl C-4), 152.9 (C-4, NC(O)), 160.9 (C-9a, C—S), 166.8 (C-3, CONS). LCMS m/z calcd for C$_{17}$H$_{13}$N$_3$O$_2$S 323 ([M+]+). found 324 ([M+H]+). HRMS m/z calcd for C$_{17}$H$_{14}$N$_3$O$_2$S 324.0807 ([M+H]+). found 324.0807. Anal. Calcd for C$_{17}$H$_{13}$N$_3$O$_2$S.HCl.2.2H$_2$O: C, 51.11; H, 4.64; N, 10.52. Found: C, 51.03; H, 4.54; N, 10.67. Analytical HPLC: tR=4.98 min.

Example 4

7-(2,6-Dimethylpyridin-4-yl)-9-ethyl-1-thia-2,4a-diaza-cyclopenta[b]naphthalene-3,4-dione hydrochloride (9)

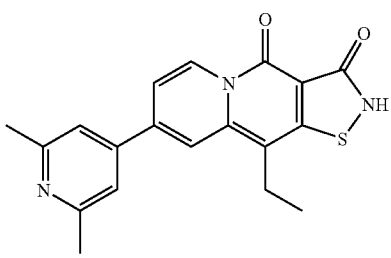

Tetrakis(triphenylphosphine)palladium(0) (25.9 mg, 0.022 mmol), 2,6-dimethyl-4-pyridinylboronic acid (112.8 mg, 0.747 mmol), and a 1 M aqueous solution of sodium bicarbonate (2.3 mL, 2.3 mmol) are added sequentially under an atmosphere of argon, to a solution containing 7-chloro-9-ethyl-1-thia-2,4a-diazacyclopenta[b]naphthalene-3,4-dione (42.0 mg, 0.150 mmol) and dimethylformamide (4.0 mL). The resulting orange mixture is irradiated in a microwave for 15 min (110° C.; 300 W) to give a red mixture. The solvent is evaporated under reduced pressure (~10 mm Hg, 50° C.), and the remaining solid washed with diethyl ether (3×15 mL). The product is extracted from this solid using hot dimethyl sulfoxide (5×2 mL) and purified by preparative HPLC. The purified product is isolated as the trifluoroacetate salt and converted to the hydrochloride salt by addition of a solution of hydrogen chloride (~1.25 M in methanol) followed by evaporation to give a deep red solid; this process is repeated twice.

Purity by HPLC: 99.6%; tR=5.80 min. mp 279-280° C. dec. $^1$H NMR (DMSO-d6): δ 1.21 (t, J=7.5 Hz, 3H, CH$_2$CH$_3$), 2.80 (s, 6H, pyridinyl CH$_3$), 2.96 (q, J=7.5 Hz, 2H, CH$_2$CH$_3$), 7.45 (dd, J=8.0 Hz, J=1.5 Hz, 1H, pyridone H-6), 8.20 (br s, 1H, pyridone H-8), 8.28 (s, 2H, pyridinyl H-3/H-5), 8.96 (d, J=8.0 Hz, 1H, pyridone H-5). LCMS m/z calcd for C$_{19}$H$_{17}$N$_3$O$_2$S 351 ([M+]). found 352 ([M+H]+). HRMS m/z calcd for C19H18N3O2S 352.1120 ([M+H]+). found 352.1120.

Example 5

7-(4-Aminomethylphenyl)-9-ethyl-1-thia-2,4a-diaza-cyclopenta[b]naphthalene-3,4-dione (10)

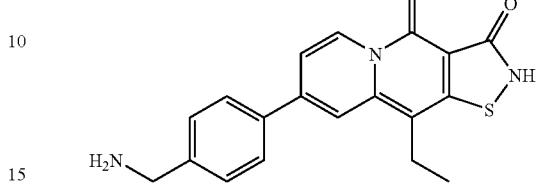

Under an atmosphere of argon, tetrakis(triphenylphosphine)palladium(0) (20.4 mg, 0.018 mmol), 4-aminomethylphenylboronic acid (110.0 mg, 0.587 mmol), and a 1 M aqueous solution of sodium bicarbonate (1.75 mL, 1.75 mmol) were added sequentially to a solution containing 7-chloro-9-ethyl-1-thia-2,4a-diazacyclopenta[b]naphthalene-3,4-dione (33.0 mg, 0.118 mmol) and dimethylformamide (3.0 mL). The resulting orange mixture was irradiated in a microwave for 15 min (110° C.; 300 W) to give a red mixture. The solvent is evaporated under reduced pressure (~10 mm Hg, 50° C.), and the remaining orange solid is washed with diethyl ether (3×15 mL).

LCMS (APCI) m/z calcd for C$_{19}$H$_{17}$N$_3$O$_2$S 351 ([M+]). found 352 ([M+H]+, 12%), 335 (100%).

$^1$H NMR (acetic acid-d4): δ 1.32 (t, J=7.5 Hz, 3H, CH$_2$CH$_3$), 2.90 (q, J=7.5 Hz, 2H, CH$_2$CH$_3$), 4.36 (s, 2H, CH$_2$N), 7.49 (dd, J=8.0 Hz, J=1.5 Hz, 1H, pyridone H-6), 7.69 (d, J=8.5 Hz, AA' part of AA'XX' spin system, 2H, phenyl H-3 and H-5), 7.91 (d, J=8.5 Hz, XX' part of AA'XX' spin system, 2H, phenyl H-2 and H-6), 7.94 (d, J=1.5 Hz, 1H, pyridone H-8), 9.24 (d, J=8.0 Hz, 1H, pyridone H-5).

Analytical HPLC: tR=6.86 min.

Example 6

Preparation of 1-Thia-2,4a,8-triaza-cyclopenta[b]naphthalene-diones

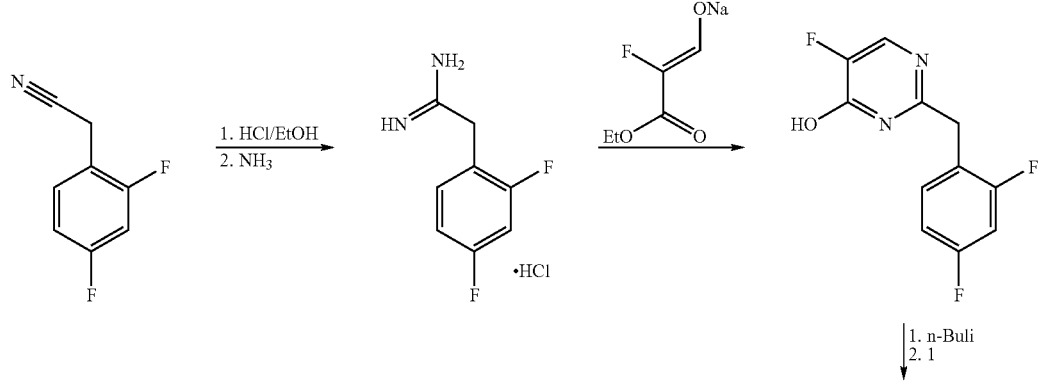

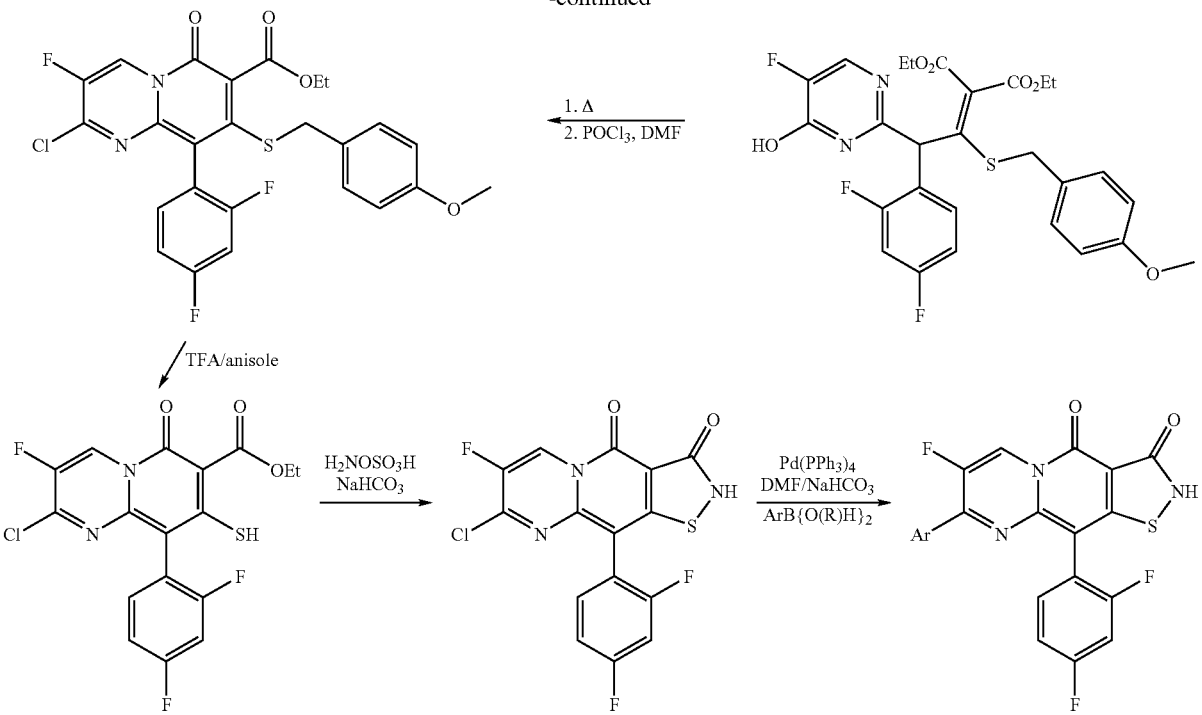

Example 7

Additional 1-thia-2,4a-diaza-cyclopenta[b]naphthalene-3,4-diones

Additional compounds of Formula I are prepared by the methods illustrated in Examples 1. Compounds of Formula I may also be prepared by the method disclosed by Otten, P. A. et al. (Bioconjugate Chem., 12: 203-212 (2001) which is hereby incorporated by reference for its teachings regarding the preparation of C—C bond at C-7 of the pyridone via Suzuki cross-coupling.

Additional compounds of Formula I are listed in Table I.

TABLE 1

| Cpd. # | Structure | Name |
|---|---|---|
| 11 | 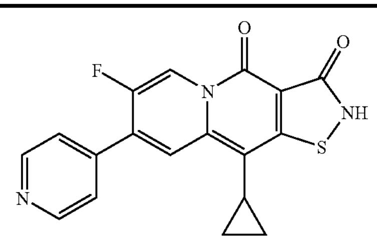 | 9-Cyclopropyl-6-fluoro-7-pyridin-4-yl-1-thia-2,4a-diaza-cyclopenta[b]naphthalene-3,4-dione |
| 12 | 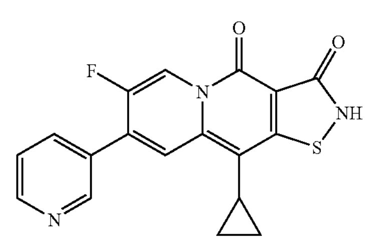 | 9-Cyclopropyl-6-fluoro-7-pyridin-3-yl-1-thia-2,4a-diaza-cyclopenta[b]naphthalene-3,4-dione |

TABLE 1-continued

| Cpd. # | Structure | Name |
|---|---|---|
| 13 | 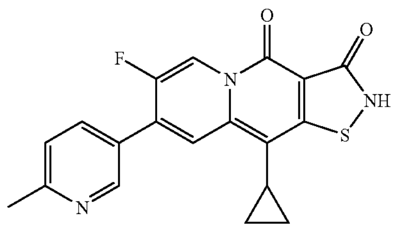 | 9-Cyclopropyl-6-fluoro-7-(6-methyl-pyridin-3-yl)-1-thia-2,4a-diaza-cyclopenta[b]naphthalene-3,4-dione |
| 14 | 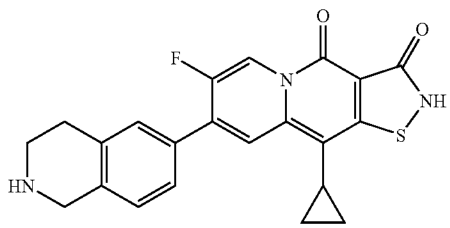 | 9-Cyclopropyl-6-fluoro-7-(1,2,3,4-tetrahydro-isoquinolin-6-yl)-1-thia-2,4a-diaza-cyclopenta[b]naphthalene-3,4-dione |
| 15 | 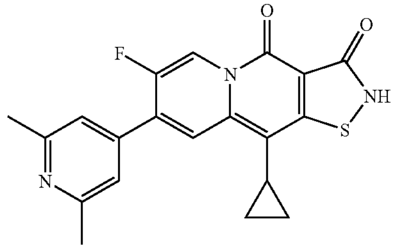 | 9-Cyclopropyl-7-(2,6-dimethyl-pyridin-4-yl)-6-fluoro-1-thia-2,4a-diaza-cyclopenta[b]naphthalene-3,4-dione |
| 16 | 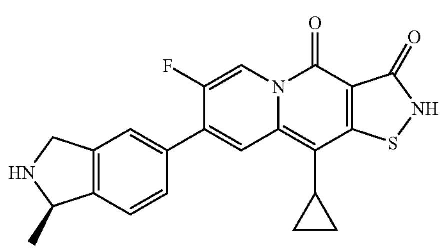 | 9-Cyclopropyl-6-fluoro-7-(1-methyl-2,3-dihydro-1H-isoindol-5-yl)-1-thia-2,4a-diaza-cyclopenta[b]naphthalene-3,4-dione |
| 17 | 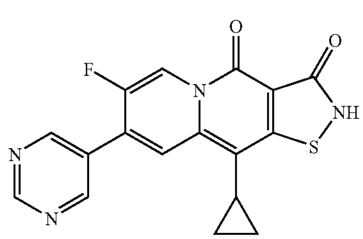 | 9-Cyclopropyl-6-fluoro-7-pyrimidin-5-yl-1-thia-2,4a-diaza-cyclopenta[b]naphthalene-3,4-dione |

TABLE 1-continued

| Cpd. # | Structure | Name |
|---|---|---|
| 18 | 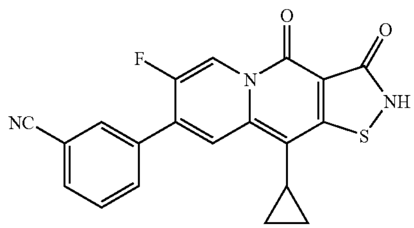 | 3-(9-Cyclopropyl-6-fluoro-3,4-dioxo-2,3-dihydro-4H-1-thia-2,4a-diaza-cyclopenta[b]naphthalen-7-yl)-banzonitrile |
| 19 | 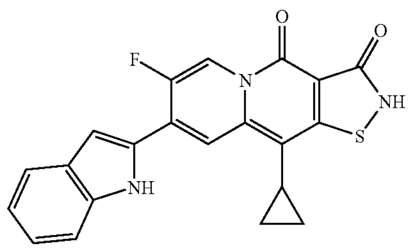 | 9-Cyclopropyl-6-fluoro-7-(1H-indol-2-yl)-1-thia-2,4a-diaza-cyclopenta[b]naphthalene-3,4-dione |
| 20 | 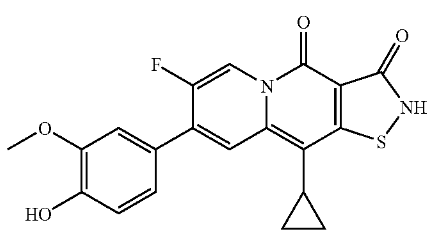 | 9-Cyclopropyl-6-fluoro-7-(4-hydroxy-3-methoxy-phenyl)-1-thia-2,4a-diaza-cyclopenta[b]naphthalene-3,4-dione |
| 21 | 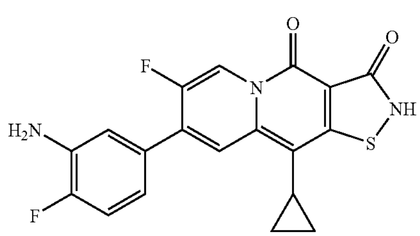 | 7-(3-Amino-4-fluoro-phenyl)-9-cyclopropyl-6-fluoro-1-thia-2,4a-diaza-cyclopenta[b]naphthalene-3,4-dione |
| 22 | 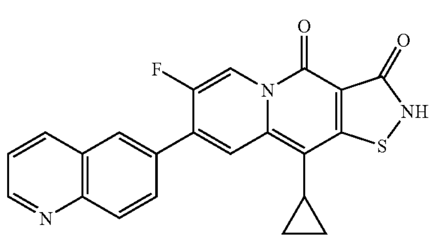 | 9-Cyclopropyl-6-fluoro-7-quinolin-6-yl-1-thia-2,4a-diaza-cyclopenta[b]naphthalene-3,4-dione |

TABLE 1-continued

| Cpd. # | Structure | Name |
|---|---|---|
| 23 | 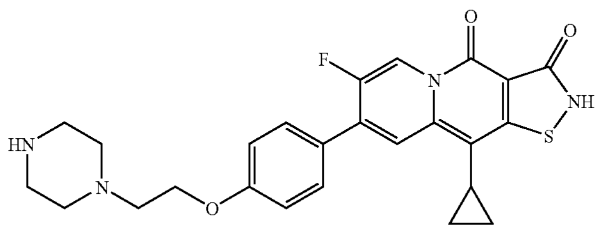 | 9-Cyclopropyl-6-fluoro-7-[4-(2-piperazin-1-yl-ethoxy)-phenyl]-1-thia-2,4a-diaza-cyclopenta[b]naphthalene-3,4-dione |
| 24 | 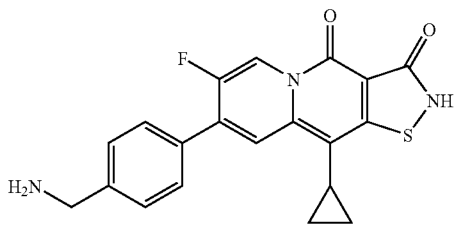 | 7-(4-Aminomethyl-phenyl)-9-cyclopropyl-6-fluoro-1-thia-2,4a-diaza-cyclopenta[b]naphthalene-3,4-dione |
| 25 | 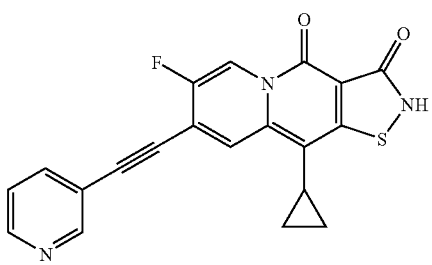 | 9-Cyclopropyl-6-fluoro-7-pyridin-3-tlethynyl-1-thia-2,4a-diaza-cyclopenta[b]naphthalene-3,4-dione |
| 26 | 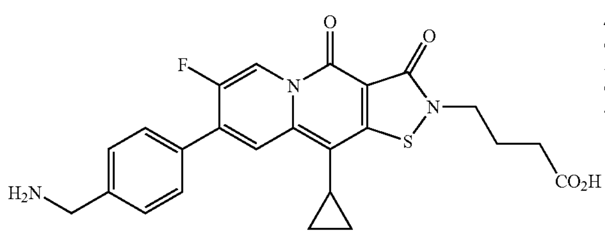 | 4-[7-(4-Aminomethyl-phenyl)-9-cyclopropyl-6-fluoro-3,4-dioxo-3H,4H-1-thia-2,4a-diaza-cyclopenta[b]naphthalene-2-yl]-butyric acid |
| 27 | 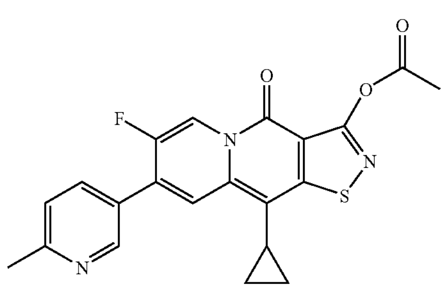 | Acetic acid 9-cyclopropyl-6-fluoro-7-(6-methyl-pyridin-3-yl)-4-oxo-4H-1-thia-2,4a-diaza-cyclopenta[b]naphthalen-3-yl ester |

TABLE 1-continued

| Cpd. # | Structure | Name |
|---|---|---|
| 28 | 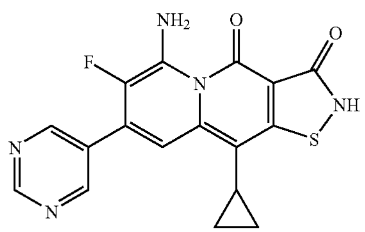 | 5-Amino-9-cyclopropyl-6-fluoro-7-pyrimidin-5-yl-1-thia-2,4a-diaza-ccyclopenta[b]naphthalene-3,4-dione |
| 29 | 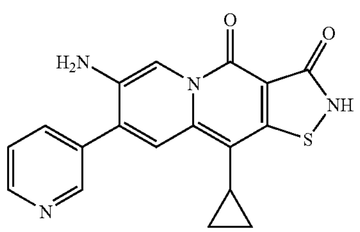 | 6-Amino-9-cyclopropyl-7-pyridin-3-yl-1-thia-2,4a-diaza-ccyclopenta[b]naphthalene-3,4-dione |
| 30 | 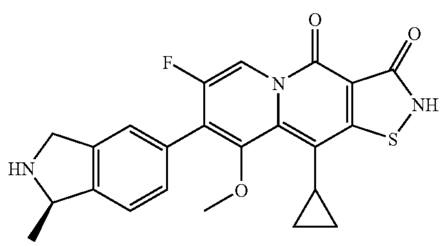 | 9-Cyclopropyl-6-fluoro-8-methoxy-7-(1-methyl-2,3-dihydro-1H-isoindol-5-yl)-1-thia-2,4a-diaza-cyclopenta[b]naphthalene-3,4-dioned |
| 31 | 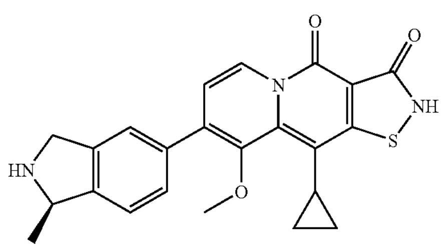 | 9-Cyclopropyl-8-methoxy-7-(1-methyl-2,3-dihydro-1H-isoindol-5-yl)-1-thia-2,4a-diaza-cyclopenta[b]naphthalene-3,4-dione |
| 32 | 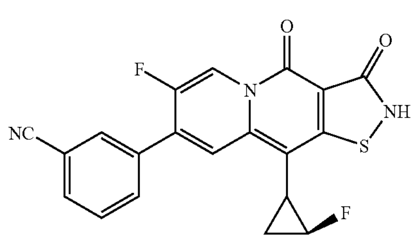 | 3-[6-Fluoro-9-(2-fluoro-cyclopropyl)-3,4-dioxo-2,3-dihydro-4H-1-thia-2,4a-diaza-cyclopenta[b]naphthalen-7-yl]-benzonitrile |

TABLE 1-continued

| Cpd. # | Structure | Name |
|---|---|---|
| 33 | 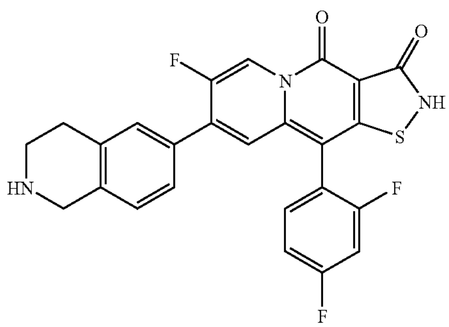 | 9-(2,4-Difluoro-phenyl)-6-fluoro-7-(1,2,3,4-tetrahydro-issoquinolin-6-yl)-1-thia-2,4a-diaza-cyclopenta[b]naphthalene-3,4-dione |
| 34 | 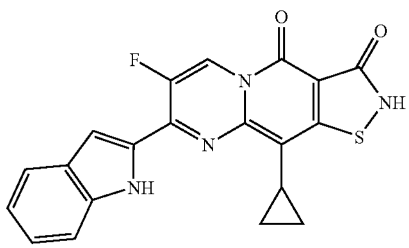 | 9-Cyclopropyl-6-fluoro-7-(1H-indol-2-yl)-1-thia-2,4a,8-triaza-cyclopenta[b]naphthalene-3,4-dione |
| 35 | 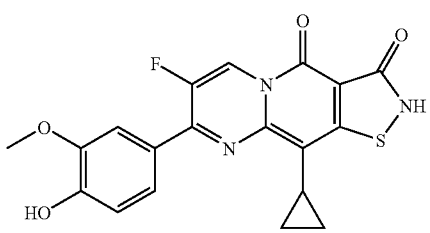 | 9-Cyclopropyl-6-fluoro-7-(4-hydroxy-3-methoxy-phenyl)-1-thia-2,4a,8-triaza-cyclopenta[b]naphthalene-3,4-dione |
| 36 | 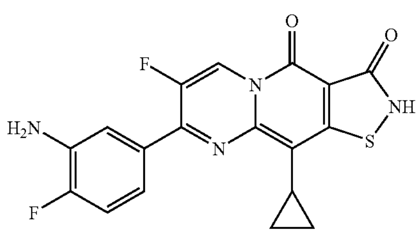 | 7-(3-Amino-4-fluoro-phenyl)-9-ccyclopropyl-6-fluoro-1-thia-2,4a,8-triaza-cyclopenta[b]naphthalene-3,4-dione |

Additionally the invention includes the following compounds of Formula A, B, C, and D:

Formula A

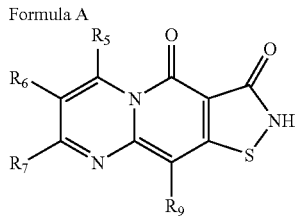

Formula B

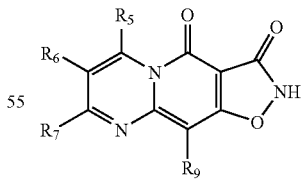

Formula C

-continued

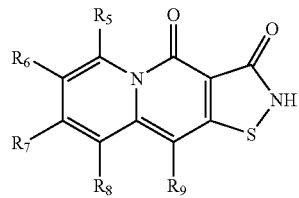

Formula D

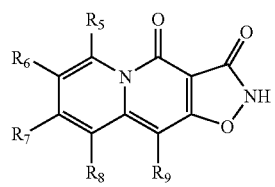

The arrays provided below disclose compounds of the general Formula A, B, C, and D in the above table.

The values "$R_5$" in these compounds are found in Array R5.
The values "$R_6$" in these compounds are found in Array R6.
The values "$R_7$" in these compounds are found in Array R7.
The values "$R_8$" in these compounds are found in Array R8.
The values "$R_9$" in these compounds are found in Array R9.

Each combination of 1 element from each of Array R5, Array R6, Array R7, Array R8, and Array R9 specifically discloses a discrete compound of the invention.

For example [$R_5$-1][$R_6$-2][$R_7$-33][$R_9$-19] of Formula A is

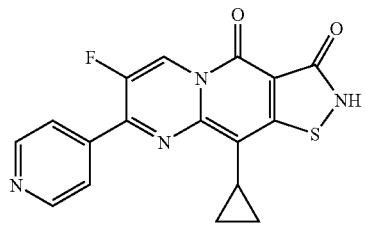

9-Cyclopropyl-6-fluoro-7-pyridin-4-yl-1-thia-2,4a,8-diaza-cyclopenta[b]naphthalene-3,4-dione

| ARRAY $R_5$ | | |
|---|---|---|
| *—H | *—F | *—Cl |
| $R_5$-1 | $R_5$-2 | $R_5$-3 |
| *—Br | *—I | *—OH |
| $R_5$-4 | $R_5$-5 | $R_5$-6 |
| *—CN | *—$NH_2$ | *—$NO_2$ |
| $R_5$-7 | $R_5$-8 | $R_5$-9 |
| *—$NHNH_2$ | *—$CH_3$ | *—$CH_2CH_3$ |
| $R_5$-10 | $R_5$-11 | $R_5$-12 |
| *—$CH_2CH_2CH_3$ | *—$CH_2CH_2CH_2CH_3$ | *—$OCH_3$ |
| $R_5$-13 | $R_5$-14 | $R_5$-15 |
| *—$OCH_2CH_3$ | *—$OCH_2CH_2CH_3$ | *—$OCH_2CH_2CH_2CH_3$ |
| $R_5$-16 | $R_5$-17 | $R_5$-18 |
| *—$NHCH_3$ | *—$NHCH_2CH_3$ | *—$NHCH_2CH_2CH_3$ |
| $R_5$-19 | $R_5$-20 | $R_5$-21 |
| *—$NHCH_2CH_2CH_2CH_3$ | *—$N(CH_3)_2$ | *—$N(CH_2CH_3)_2$ |
| $R_5$-22 | $R_5$-23 | $R_5$-24 |
| *—$N(CH_2CH_2CH_3)_2$ | *—$N(CH_2CH_2CH_2CH_3)_2$ | *—$NHNHCH_3$ |
| $R_5$-25 | $R_5$-26 | $R_5$-27 |
| *—$NHNHCH_2CH_3$ | *—$NHNHCH_2CH_2CH_3$ | *—$NHNHCH_2CH_2CH_2CH_3$ |
| $R_5$-28 | $R_5$-29 | $R_5$-30 |
| *—$NHN(CH_3)_2$ | *—$NHN(CH_2CH_3)_2$ | *—$NHN(CH_2CH_2CH_3)_2$ |
| $R_5$-31 | $R_5$-32 | $R_5$-33 |
| *—$NHN(CH_2CH_2CH_2CH_3)_2$ | | |
| $R_5$-34 | | |

| ARRAY $R_6$ | | |
|---|---|---|
| *—H | *—F | *—Cl |
| $R_6$-1 | $R_6$-2 | $R_6$-3 |
| *—Br | *—I | *—OH |
| $R_6$-4 | $R_6$-5 | $R_6$-6 |
| *—CN | *—$NH_2$ | *—$CH_3$ |
| $R_6$-7 | $R_6$-8 | $R_6$-9 |
| *—$CH_2CH_3$ | *—$CH_2CH_2CH_3$ | *—$CH_2CH_2CH_3$ |
| $R_6$-10 | $R_6$-11 | $R_6$-12 |
| *—$OCH_3$ | *—$OCH_2CH_3$ | *—$OCH_2CH_2CH_3$ |

-continued

ARRAY R₆

| | | |
|---|---|---|
| R₆-13 *—OCH₂CH₂CH₃ | R₆-14 *—NHCH₃ | R₆-15 *—NHCH₂CH₃ |
| R₆-16 *—NHCH₂CH₂CH₃ | R₆-17 *—NHCH₂CH₂CH₃ | R₆-18 *—N(CH₃)₂ |
| R₆-19 *—N(CH₂CH₃)₂ | R₆-20 *—N(CH₂CH₂CH₃)₂ | R₆-21 *—N(CH₂CH₂CH₂CH₃)₂ |
| R₆-22 *—CF₃ | R₆-23 *—OCF₃ | R₆-24 |
| R₆-25 | R₆-26 | |

ARRAY R₇

| | | | | | |
|---|---|---|---|---|---|
| *—Cl | | R₇-1 *—Br | R₇-2 *—I | R₇-3 |
| *—O(SO₂)CF₃ | | R₇-4 *—N₂BF₄ | R₇-5 *—CH₃ | R₇-6 |
| *—CH₂CH₃ | | R₇-7 *—CH₂CH₂ | R₇-8 *—CH₂CH₂CH₃ | R₇-9 |
| *—CH₂CH₂CH₂CH₃ | | R₇-10 *—CH₂CH₂CH₂CH₂CH₃ | R₇-11 *—CH₂CH₂CH₂CH₂CH₂CH₃ | R₇-12 |
| *—CH=CHCH₃ | | R₇-13 *—CH=CHCH₂CH₃ | R₇-14 *—CH=CHCH₂CH₂CH₃ | R₇-15 |
| *—(C=O)—CH₃ | | R₇-16 *—(C=O)—CH₂CH₃ | R₇-17 *—(C=O)—CH₂CH₂CH₃ | R₇-18 |
| *—(C=O)NH—CH₃ | | R₇-19 *—C(=O)NH—CH₂CH₃ | R₇-20 *—(C=O)NH—CH₂CH₂CH₃ | R₇-21 |
| *—C≡C—CH₃ | | R₇-22 *—C≡C—CH₂CH₃ | R₇-23 *—C≡C—CH₂CH₂CH₃ | R₇-24 |

(cyclopropyl) R₇-25, (cyclobutyl) R₇-26, (cyclopentyl) R₇-27

(cyclohexyl) R₇-28, (cycloheptyl) R₇-29, (cyclopropenyl) R₇-30

(cyclopentadienyl) R₇-31, (phenyl) R₇-32, (4-pyridyl) R₇-33

(3-pyridyl) R₇-34, (6-methyl-3-pyridyl) R₇-35, (2,6-dimethyl-4-pyridyl) R₇-36

(5-pyrimidinyl) R₇-37, (1,2,3,4-tetrahydroisoquinolin-6-yl) R₇-38, (isoindolin-5-yl) R₇-39

(indolin-2-yl) R₇-40, (3-cyanophenyl) R₇-41, (3-methoxy-4-hydroxyphenyl) R₇-42

-continued

ARRAY R₇

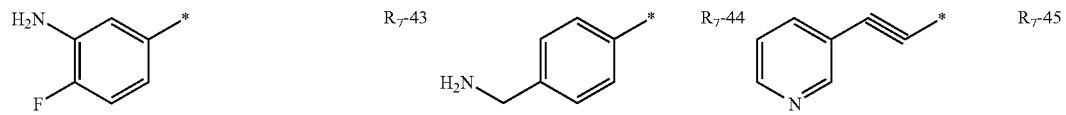

R₇-43, R₇-44, R₇-45

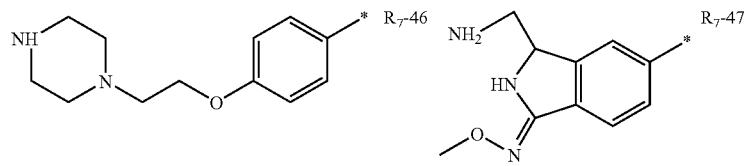

R₇-46, R₇-47

ARRAY R₈

| | | |
|---|---|---|
| *—H  R₈-1 | *—F  R₈-2 | *—Cl  R₈-3 |
| *—Br  R₈-4 | *—I  R₈-5 | *—OH  R₈-6 |
| *—CN  R₈-7 | *—NH₂  R₈-8 | *—NO₂  R₈-9 |
| *—NHNH₂  R₈-10 | *—CH₃  R₈-11 | *—CH₂CH₃  R₈-12 |
| *—CH₂CH₂CH₃  R₈-13 | *—CH₂CH₂CH₂CH₃  R₈-14 | *—OCH₃  R₈-15 |
| *—OCH₂CH₃  R₈-16 | *—OCH₂CH₂CH₃  R₈-17 | *—OCH₂CH₂CH₂CH₃  R₈-18 |
| *—NHCH₃  R₈-19 | *—NHCH₂CH₃  R₈-20 | *—NHCH₂CH₂CH₃  R₈-21 |
| *—NHCH₂CH₂CH₂CH₃  R₈-22 | *—NHNHCH₃  R₈-23 | *—NHNHCH₂CH₃  R₈-24 |
| *—NHNHCH₂CH₂CH₃  R₈-25 | *—NHNHCH₂CH₂CH₂CH₃  R₈-26 | *—NHN(CH₃)₂  R₈-27 |
| *—NHN(CH₂CH₃)₂  R₈-28 | *—NHN(CH₂CH₂CH₃)₂  R₈-29 | *—NHN(CH₂CH₂CH₂CH₃)₂  R₈-30 |
| *—CF₃  R₈-31 | *—OCF₃  R₈-32 | |

ARRAY R₉

| | | | | | |
|---|---|---|---|---|---|
| *—CH₃ | R₉-1 | *—CH₂CH₃ | R₉-2 | *—CH₂CH₂CH₃ | R₉-3 |
| *—CH₂CH₂CH₂CH₃ | R₉-4 | *—(CH₂)₄CH₃ | R₉-5 | *—(CH₂)₅CH₃ | R₉-6 |
| *—(CH₂)₆CH₃ | R₉-7 | *—(CH₂)₇CH₃ | R₉-8 | *—OCH₃ | R₉-9 |
| *—OCH₂CH₃ | R₉-10 | *—OCH₂CH₂CH₃ | R₉-11 | *—OCH₂CH₂CH₂CH₃ | R₉-12 |
| *—NHCH₃ | R₉-13 | *—NHCH₂CH₃ | R₉-14 | *—NHCH₂CH₂CH₃ | R₉-15 |
| *—NHCH₂CH₂CH₂CH₃ | R₉-16 | *—NH(CH₃)₂ | R₉-17 | *—NH(CH₂CH₃)₂ | R₉-18 |

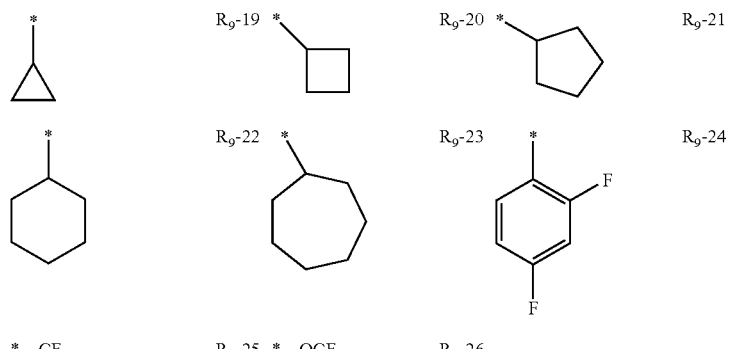

R₉-19, R₉-20, R₉-21, R₉-22, R₉-23, R₉-24

| | | | |
|---|---|---|---|
| *—CF₃ | R₉-25 | *—OCF₃ | R₉-26 |

Example 8

X-ray Crystal Structure of 7-Chloro-9-ethyl-1-thia-2,4a-diazacyclopenta[b]naphthalene-3,4-dione (6)

Data Collection

A yellow blade crystal of $C_{12}H_9ClN_2O_2S$ having approximate dimensions of 0.25×0.10×0.10 mm$^3$ was mounted with epoxy cement on the tip of a fine glass fiber. All measurements were made on a Nonius KappaCCD diffractometer with graphite monochromated Mo—Kα radiation.

Cell constants and an orientation matrix for data collection corresponded to a primitive monoclinic cell with dimensions:
a=7.0574(14) Å
b=9.950(2) Å
c=16.661(3) Å
V=1165.6(4) Å$^3$
α=90°
β=94.96(3)°
γ=90°

For Z=4 and F.W.=280.72, the calculated density is 1.600 g/cm$^3$. Based on a statistical analysis of intensity distribution, and the successful solution and refinement of the structure, the space group was determined to be P2$_1$/c (#14).

The data were collected at a temperature of 173(2) K to a maximum 2θ value of 56.54°. Five omega scans consisting of 37, 29, 34, 14, and 17 data frames, respectively, were collected with a frame width of 2.0° and a detector-to-crystal distance, Dx, of 35.0 mm. Each frame was exposed twice (for the purpose of de-zingering) for a total of 40s. The data frames were processed and scaled using the DENZO software package.

Data Reduction

A total of 4725 reflections were collected of which 2872 were unique and observed ($R_{int}$=0.0321). The linear absorption coefficient, μ, for Mo—Kα radiation is 5.00 cm$^{-1}$, and no absorption correction was applied. The data were corrected for Lorentz and polarization effects.

Structure Solution and Refinement

The structure was solved by direct methods and expanded using Fourier techniques. The non-hydrogen atoms were refined anisotropically, and hydrogen atoms, with exceptions noted, were treated as idealized contributions. The final cycle of full-matrix least-squares refinement$^3$ on F was based on 2872 observed reflections (I>2.00σ(I)) and 167 variable parameters and converged with unweighted and weighted agreement factors of:

$$R=\Sigma||Fo|-|Fc||/\Sigma|Fo|=0.0406$$

$$R_w=\{\Sigma[w(F_o^2-F_c^2)^2]/\Sigma[w(F_o^2)^2]\}^{1/2}=0.1030$$

The maximum and minimum peaks on the final difference Fourier map corresponded to 0.324 and −0.347 e$^-$/Å$^3$ respectively.

Example 9

Antimicrobial Activity of Compounds of the Invention

The antimicrobial activity of the compounds of the invention may be evaluated by a number of methods, including the following visual minimum inhibitory concentration (MIC) assay. This assay determines the minimum concentration of compound required to inhibit growth of a bacterial strain.

Minimum Inhibitory Concentration (MIC) Assay

Whole-cell antibacterial activity is determined by broth microdilution using conditions recommended by the National Committee for Clinical Laboratory Standards (NCCLS). The minimum inhibitory concentration (MIC) was defined as the lowest concentration of antimicrobial agent to completely inhibit visible growth after 18-24 h at 37° C.

Test compounds are dissolved in DMSO and diluted 1:50 in Mueller-Hinton II broth (Becton-Dickinson) to produce a 256 μg/ml stock solution. In a 96-well microtiter plate, the compound solution is serially two-fold diluted in Mueller-Hinton II broth. After the compounds are diluted, a 50 μg aliquot of the test organism (~1×10$^6$ cfu/mL) is added to each well of the microtiter plate. The final test concentrations range from 0.125-128 μg/mL. Inoculated plates are incubated in ambient air at 37° C. for 18 to 24 hours. The organisms selected for testing included laboratory strains *S. aureus* ATCC 29213 and *E. coli* ATCC 25922 (strains purchased from American Type Culture Collection, Manassas, Va.). The minimum inhibitory concentration (MIC) was determined as the lowest concentration of compound that inhibited visible growth of the test organism.

Topoisomerase IV Activity

Enzyme activity is measured by a decatenation assay that monitors the ATP-dependent unlinking of DNA minicircles from kinetoplast DNA. Analysis is done by gel electrophoresis through 1% agarose/TBE gel. DNA is visualized with an Alpha Imager 2200 Analysis System and the IC$_{50}$ determined by nonlinear regression analysis with Graphpad Prism software. *S. aureus* topoismerase IV enzyme subunits, grlA and grlB, are purified to homogeneity from over-expression plasmids in *E. coli*.

DNA Gyrase Activity

Enzyme activity is measured by a supercoiling assay that monitors the ATP-dependent conversion of relaxed pBR$_{322}$ DNA to the supercoiled form. Analysis is done by gel electrophoresis through 1% agarose/TBE gel. DNA is visualized with an Alpha Imager 2200 Analysis System and the IC$_{50}$ determined by nonlinear regression analysis with Graphpad Prism software. *E. coli* DNA gyrase enzyme subunits, gyrA and gyrB, are purified to homogeneity from over-expression constructs in *E. coli*.

Human Topoisomerase II Activity

Enzyme activity is measured by a DNA cleavage assay that monitors generation of linear DNA from supercoiled pBR$_{322}$ DNA. Human p170 topoisomerase II is purchased from TopoGen. Analysis is done by electrophoresis through 1% agarose/TAE gel with 0.5 μg/mL ethidium bromide, followed by visualization and quantification with Alpha Imager 2200. The EC$_2$ value is defined as the effective concentration of drug required to enhance enzyme-mediated cleavage of double-stranded DNA twofold.

Compounds 8 and 9 exhibit an MIC of 10 μg/ml against *S. aureaus* and *E. coli* when tested in the above assay for minimal inhibitory activity. These compounds also exhibit inhibition of e. coli DNA gyrase supercoiling (IC$_{50}$<1 μM) and inhibition of *S. aureus* topoisomerase IV activity (IC$_{50}$ <10 μM). Compounds 8 and 9 do not inhibit *S. aureus* DNA gyrase supercoiling activity (IC$_{50}$>200 μM) and do not display activity against human topoisomerase II (EC2>150 μM). EC2 is the effective concentration of drug required to enhance enzyme-mediated cleavage of double-stranded DNA.

Example 10

Cell Viability Staining with Alamar Blue

To determine whether the microcidal effect observed against *S. aureus* and *E. coli* is specific to bacterial cells, compounds are screened for cell viability effects on several human cell types.

Optimal cell density is first determined by plating cells in a 96-well plate standard sterile tissue culture plates in 100 µl media, 10% FBS at six cell densities from 500 cells/well to 15,000 cells/well. A cell free well containing only media is used as a control. Cells are incubated at 37° C. in a 5% $CO_2$ incubator for 24 hours. 10% culture volume (10 microliters) of Alamar Blue (Biosource, DAL 1100, 100 mL) is then added. Cells are incubated at 37° C. in a 5% $CO_2$ incubator and read in a Victor V plate reader, 544 nm excitation, 590 nm emission, at 3, 4, and 24 hours after the addition of Alamar Blue. The cell number vs. change in fluorescence is plotted to determine linearity of signal vs. cell number. The optimal density varies between 500-15,000 cells/well depending on the specific cell type. The optimal density is selected based on the highest number of cells that is still in the linear response range.

Determination of Compound Cytotoxicity

Cells are plated at optimal cell density in a standard sterile tissue culture 96 well plate, and incubated at 37° C. O/N in a 5% CO2 incubator. 12 to 48 hours post-plating media is removed. The cells are washed 1 or 2 times with 1×PBS and replaced with fresh media containing the test compound in 1% DMSO. 24 to 72 hours after addition of compound, the media is removed, and the cells washed 1 to 2 times with 1×PBS. Fresh media containing 1/10 volume of Alamar Blue is then added. Plates are incubated 4 hours at 37° C. in a 5% CO2 incubator and read in a Victor V plate reader, 544 nm excitation, 590 nm emission.

Compounds are diluted to 20 micromolar in 1% DMSO and media and screened in duplicate to obtain single concentration cytotoxicity data. Eight concentration points from 0.78 micromolar to 100 micromolar, run in duplicate, are used to determine cyctotoxicity CC50 values. Cells with 1% DMSO and media are used as a negative control, compounds having a known CC50 against a particular cell type are used as positive controls.

The change in fluorescence vs. concentration of test compound is plotted to determine the cytotoxicity of the compound.

Sample media conditions, optimal plating densities, and positive control compounds for two cell types screened are presented in Table II.

Preferred compounds disclosed in Example 1 and 3 to 6 exhibit CC50 values greater than 10 uM against each of the cell lines listed below. Other cell types that may be used include but are not limited to Balb/3TC, CEM-SS, HeLa, HepG2, HT-29, MRC-5, SK-N—SH, U-87 MG, 293T, and Huh-7. More preferred are compounds with a $CC_{50}$ value greater than 50 uM. Most preferred are compounds with a $CC_{50}$ value greater than 100 uM.

TABLE II

| CELL LINE | MEDIA | PLATING DENSITY | POSITIVE CONTROL |
|---|---|---|---|
| CHO (Chinese hamster ovary) | 1. F-12 Nutrient Mixture (Gibco #11765-054) containing 10% FBS, 1% Pen Strep, 1.5 g/L Sodium Bicarbonate 2. McCoy's 5a medium, 10% FBS and PS/Gln | 7,000 cells/well | Terfenadine $CC_{50}$ = 4.3-6.5 µM |
| HEP 2 (laryngeal carcinoma) | Minimum Essential Medium - Alpha Medium (Gibco # 12571-063) containing 10% FBS, 1% Pen Strep, 1.5 g/L Sodium Bicarbonate | 7,000 cells/well | Terfenadine $CC_{50}$ = 3-5 µM |

Example 11

Pharmmaceutical Formulations

Examples 11A through 11D are examples of pharmaceutical compositions containing the compounds of Formula I. The abbreviation 'A.M.' stands for an antimicrobial compound of the present invention.

Example 11A

Capsules 20 grams of the A.M., 6 grams sodium lauryl sulfate, 56 grams starch, 56 grams lactose, 0.8 grams colloidal silicon dioxide, and 1.2 grams magnesium stearate are vigorously stirred together. The resulting mixture is subsequently filled into 1000 suitable hardened gelatin capsules, comprising each 20 mg of the active ingredient.

Example 11B

Film-Coated Tablets

Preparation of tablet core: A mixture of 10 grams of the A.M., 57 grams lactose and 20 grams starch is mixed well and thereafter humidified with a solution of 0.5 grams sodium dodecyl sulfate, and 1.0 grams polyvinylpyrrolidone (KOLLIDON-K 90) in about 20 ml of water. The wet powder mixture is sieved, dried, and sieved again. Then 100 grams microcrystalline cellulose (AVICEL) and 15 grams hydrogenated vegetable oil (STEROTEX) are added. The whole is mixed well and compressed into tablets, giving 1000 tablets, each containing 10 mg of the active ingredient.

Coating: Ethyl cellulose (0.5 grams, ETHOCEL 22 CPS) in 15 ml of dichloromethane is added to a solution of 1.0 grams methyl cellulose (Methocel 60 HG.RTM.) in 7.5 ml of denatured ethanol. Then 7.5 ml of dichloromethane and 0.25 ml 1,2,3-propanetriol are added. Polyethylene glycol (1.0 grams) is melted and dissolved in 7.5 ml of dichloromethane and added to the cellulose-containing solution. Magnesium Octadecanoate (0.25 grams), 0.5 grams polyvinylpyrrolidone, and 3.0 ml of concentrated color suspension (OPASPRAY K-1-2109) are added and the whole mixture homogenized. The tablet cores are coated with this mixture in a coating apparatus.

Example 11C

Injectible Solutions (i) 1.8 grams methyl 4-hydroxybenzoate and 0.2 grams propyl 4-hydroxybenzoate are dissolved in about 0.5 L of boiling water. After cooling to about 50° C., 4 grams lactic acid, 0.05 grams propylene glycol, and 4 grams of the A.M are added while stirring. The solution is cooled to room temperature and supplemented with water for injection q.s. giving a solution containing 4 mg/ml of A.M. The solution is sterilized by filtration and filled in sterile containers.

(ii) 100.0 g of an acid salt of an A.M. of the invention is dissolved in boiling water. After cooling to about 50° C., 37.5 grams lactic acid (90% by weight) are added while stirring. The solution is cooled to room temperature and water is added to 1 L. The solution is sterilized by filtration and filled in sterile containers.

(iii) 5.00 g of an acid salt of an A.M. of the invention is dissolved in boiling water. After cooling to about 50° C., 2.20 grams lactic acid (90% by weight) are added while stirring. The solution is cooled to room temperature and water is added to 100 ml.

Example 11D

Cream

Phase I contains Sorbitan monostearate (2.0 g), Polyoxyethylene (20) sorbitan monostearate (1.5 g), Synthetic spermaceti (3.0 g) Cetyl stearyl alcohol (10.0 g) and 2-Octyldodecanol (13.5 g). The phase I mixture is heated to 75° C., stirred and mixed. Phase II contains A.M. (1.0 g). Phase II is added to phase I, stirred and suspended. Phase III contains Benzyl alcohol (1.0 g) and demineralized water (q.s. 100 g). Phase III is heated to 75° C. and added to phase II. The cream is mixed intensively and cooled slowly to room temperature, with further stirring. After cooling to room temperature the cream is homogenized.

What is claimed is:

1. A compound of Formula I

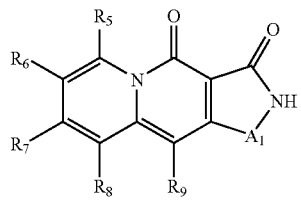

Formula I or a pharmaceutically acceptable salt thereof, wherein
$A_1$ is S, O, SO, or $SO_2$;
$R_5$ is hydrogen, halogen or amino
$R_6$ is hydrogen, halogen, or amino, cyano;
$R_7$ is $XR_A$ where
X is absent or —C≡C—, and
$R_A$ is phenyl, or a monocyclic or bicyclic 5- to 10- membered bicyclic saturated, partially unsaturated, or aromatic heterocylic group containing at least one nitrogen atom and bound via a carbon atom; each of which $R_A$ is substituted with 0 to 5 substituents independently chosen from
halogen, hydroxy, amino, cyano, $C_1$-$C_6$alkyl optionally substituted with amino, ($C_1$-$C_6$alkoxy)$C_0$-$C_4$alkyl, mono- and di-($C_1$-$C_4$)alkylamino, =$NOR_{10}$, where $R_{10}$ is $C_1$-$C_4$alkyl, and —$OR_D$, where $R_D$ is ($C_2$-$C_6$heterocycloalkyl)$C_0$-$C_2$alkyl;
$A_8$ is $CR_8$;
$R_8$ is hydrogen, $C_1$-$C_4$alkyl, $C_1$-$C_4$alkoxy; and
$R_9$ is ($C_3$-$C_7$cycloalkyl)$C_0$-$C_4$alkyl or phenyl, each of which is substituted with 0 to 3 substituents independently chosen from halogen.

2. A compound of Formula II

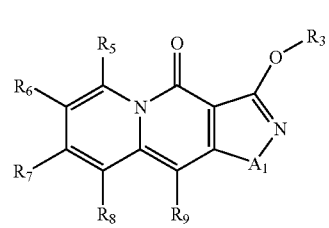

Formula II or a pharmaceutically acceptable salt thereof, wherein
$A_1$ is S, O, SO, or $SO_2$;
$R_3$ is hydrogen, $C_1$-$C_6$alkyl, $C_1$-$C_6$alkanoyl, mono- or di-$C_1$-$C_6$alkylcarbamate, or $C_1$-$C_6$alkylsulfonate; each of which is substituted with 0 to 3 substituents independently chosen from halogen, hydroxy, amino, cyano, nitro, $C_1$-$C_4$alkoxy, mono- and di-$C_1$-$C_4$alkylamino, $C_1$-$C_2$haloalkyl, and $C_1$-$C_2$haloalkoxy;
$R_5$ is hydrogen, halogen or amino;
$R_6$ is hydrogen, halogen, or amino;
$R_7$ is $XR_A$ where
X is absent or —C≡C—, and
$R_A$ is phenyl or a monocyclic or bicyclic 5- to 10- membered bicyclic saturated, partially unsaturated, or aromatic heterocylic group containing at least one nitrogen atom and bound via a carbon atom; each of which $R_A$ is substituted with 0 to 5 substituents independently chosen from halogen, hydroxy, amino, cyano, $C_1$-$C_6$alkyl optionally substituted with amino, ($C_1$-$C_6$alkoxy)$C_0$-$C_4$alkyl, mono- and di-($C_1$-$C_4$)alkylamino, =$NOR_{10}$, where $R_{10}$ is $C_1$-$C_4$alkyl, and —$OR_D$, where $R_D$ is ($C_2$-$C_6$heterocycloalkyl)$C_0$-$C_2$alkyl;
$R_8$ is hydrogen, $C_1$-$C_4$alkyl, or $C_1$-$C_4$alkoxy; and
$R_9$ is ($C_3$-$C_7$cycloalkyl)$C_0$-$C_4$alkyl, or phenyl, each of which is substituted with 0 to 3 substituents independently chosen from halogen.

3. A compound or salt of claim 1, wherein $A_1$ is S.
4. A compound or salt of claim 3 wherein $R_5$ is hydrogen.
5. A compound or salt of claim 3 wherein: $R_6$ is hydrogen, fluoro, or amino.
6. A compound or salt of claim 5 wherein $R_6$ is fluoro or hydrogen.
7. A compound or salt of claim 3 wherein $R_8$ is hydrogen or methoxy.
8. A compound or salt of claim 3 wherein $R_9$ is $C_3$-$C_7$cycloalkyl.
9. A compound or salt of claim 8 wherein $R_9$ is cyclopropyl or 2,4-difluorophenyl.
10. A compound or salt of claim 1 wherein
$R_7$ is $XR_A$ where
X is absent or —C≡C—, and
$R_A$ is phenyl, dihydroindolyl, dihydroisoindolyl, dihydroquinolinyl, dihydroisoquinolinyl, indolyl, imidazolyl, isoindolyl, isoquinolinyl, isoxazolyl, piperazinyl, piperidinyl, pyrazinyl, pyridyl, pyrirnidinyl, pyrrolidinyl, pyrrolyl, pyrazolyl, quinolinyl, quinazolinyl, quinoxalinyl, thiazolyl, tetrahydropyridinyl, tetrahydroisoquionolinyl, or tetrahydroquinolinyl; group; each of which is substituted with 0 to 5 substituents independently chosen from halogen, hydroxy, amino, cyano, $C_1$-$C_6$alkyl optionally substituted with amino, ($C_1$-$C_6$alkoxy)$C_0$-$C_4$alkyl, mono- and di-($C_1$-$C_4$)alkylamino, =$NOR_{10}$, where $R_{10}$ is $C_1$-$C_4$alkyl, and —$OR_D$, where $R_D$ is $C_2$-$C_6$heterocycloalkyl)$C_0$-$C_2$alkyl.

11. A compound or salt of claim 10 wherein $R_A$ is a phenyl, dihydroindolyl, dihydroisoindolyl, dihydroquinolinyl, dihydroisoquinolinyl, indolyl, isoindolyl, isoquinolinyl, pyridyl, pyrirnidinyl, quinolinyl, tetrahydroisoquionolinyl, or tetrahydroquinolinyl; group; each of which is substituted with 0 to 5 substituents independently chosen from halogen, hydroxy, amino, cyano, $C_1$-$C_4$alkyl, $C_1$-$C_4$alkoxy, and mono- and di-($C_1$-$C_4$)alkylamino.

12. A compound or salt of claim 11 in which X is absent.

13. A compound or salt of claim 12 in which $R_A$ is phenyl or pyridyl, each of which is substituted with 0 to 3 substituents independently chosen from halogen, hydroxy, amino, cyano, $C_1$-$C_4$alkyl, $C_1$-$C_4$alkoxy, and mono- and di-($C_1$-$C_4$)alkylamino.

14. A pharmaceutical composition comprising a compound or salt of claim 1 together with a pharmaceutically acceptable carrier, diluent, or excipient.

15. A compound or salt thereof of claim 1, wherein the compound is

9-Cyclopropyl-6-fluoro-7-pyridin-4-yl-1-thia-2,4a-diaza-cyclopenta[b]naphthalene-3,4-dione;

9-Cyclopropyl-6-fluoro-7-pyridin-3-yl-1-thia-2,4a-diaza-cyclopenta[b]naphthalene-3,4-dione;

9-Cyclopropyl-6-fluoro-7-(6-methyl-pyridin-3-yl)-1-thia-2,4a-diaza-cyclopenta[b]naphthalene-3,4-dione;

9-Cyclopropyl-6-fluoro-7-(1,2,3,4-tetrahydro-isoquinolin-6-yl)-1-thia-2,4a-diaza-cyclopenta[b]naphthalene-3,4-dione;

9-Cyclopropyl-7-(2,6-dimethyl-pyridin-4-yl)-6-fluoro-1-thia-2,4a-diaza-cyclopenta[b]naphthalene-3,4-dione;

9-Cyclopropyl-6-fluoro-7-(1-methyl-2,3-dihydro -1H-isoindol-5-yl)-1-thia-2,4a-diaza-cyclopenta[b]naphthalene-3,4-dione;

9-Cyclopropyl-6-fluoro-7-pyrimidin-5-yl-1-thia-2,4a-diaza-cyclopenta[b]naphthalene-3,4-dione;

3-(9-Cyclopropyl-6-fluoro-3,4-dioxo-2,3-dihydro-4H-1-thia-2,4a-diaza-cyclopenta[b]naphthalen-7-yl)-benzonitrile;

9-Cyclopropyl-6-fluoro-7-(1H-indol-2-yl)-1-thia-2,4a-diaza-cyclopenta[b]naphthalene-3,4-dione;

9-Cyclopropyl-6-fluoro-7-(4-hydroxy-3-methoxy-phenyl)-1-thia-2,4a-diaza -cyclopenta[b]naphthalene-3,4-dione;

7-(3-Amino-4-fluoro-phenyl)-9-cyclopropyl-6-fluoro-1-thia-2,4a-diaza-cyclopenta[b]naphthalene-3,4-dione;

9-Cyclopropyl-6-fluoro-7-quinolin-6-yl-1-thia-2,4a-diaza-cyclopenta[b]naphthalene-3,4-dione;

9-Cyclopropyl-6-fluoro-7-[4-(2-piperazin-1-yl-ethoxy)-phenyl]-1-thia-2,4a-diaza-cyclopenta[b]naphthalene-3,4-dione; (missing cmp 25)

7-(4-Aminomethyl-phenyl)-9-cyclopropyl-6-fluoro-1-thia-2,4a-diaza-cyclopenta[b]naphthalene-3,4-dione;

9-Cyclopropyl-6-fluoro-7-pyridin-3-ylethynyl-1-thia-2,4a-diaza-cyclopenta[b]naphthalene-3,4-dione;

4-[7-(4-Aminomethyl-phenyl)-9-cyclopropyl-6-fluoro-3,4-dioxo-3H,4H-1-thia-2,4a-diaza-cyclopenta[b]naphthalen-2-yl]-butyric acid;

Acetic acid 9-cyclopropyl-6-fluoro-7-(6-methyl-pyridin-3-yl)-4-oxo-4H-1-thia-2,4a-diaza-cyclopenta[b]naphthalen-3-yl ester;

5-Amino-9-cyclopropyl-6-fluoro-7-pyrimidin-5-yl-1-thia-2,4a-diaza-cyclopenta[b]naphthalene-3,4-dione;

6-Amino-9-cyclopropyl-7-pyridin-3-yl-1-thia-2,4a-diaza-cyclopenta[b]naphthalene-3,4-dione;

9-Cyclopropyl-6-fluoro-8-methoxy-7-(1-methyl-2,3-dihydro-1H-isoindol-5-yl)-1-thia-2,4a-diaza-cyclopenta[b]naphthalene-3,4-dione;

9-Cyclopropyl-8-methoxy-7-(1-methyl-2,3-dihydro -1H-isoindol-5-yl)-1-thia-2,4a-diaza-cyclopenta[b]naphthalene-3,4-dione;

3-[6-Fluoro-9-(2-fluoro-cyclopropyl)-3,4-dioxo-2,3-dihydro-4H-1-thia-2,4a-diaza-cyclopenta[b]naphthalen-7-yl]-benzonitrile; and 9-(2,4-Difluoro-phenyl)-6-fluoro-7-(1,2,3,4-tetrahydro-isoquinolin-6-yl)-1-thia-2,4a-diaza-cyclopenta[b]naphthalene-3,4-dione.

16. A compound or salt of claim 13 in which $R_A$ is a phenyl, pyridyl, pyrimidinyl, isoquinolinyl, quinolinyl, indolyl, pyrrolyl, isoindolyl, dihydroisoindolyl, tetrahydroisoquinolinyl, or tetrahydroisoquinolinyl group, each of which is substituted with 0 to 3 substituents independently chosen from halogen, hydroxy, amino, cyano, $C_1$-$C_4$alkyl, $C_1$-$C_4$alkoxy, mono- and di-(C1-$C_4$)alkylamino, $C_1$-$C_2$haloalkyl, and $C_1$-$C_2$haloalkoxy.

17. A compound or salt of claim 16 in which $R_A$ is phenyl, pyridyl-3-yl or pyrid-4-yl, each of which is substituted with 1 or 2 substituents independently chosen from fluoro, amino, hydroxy, cyano, and methyl.

18. A compound or salt of claim 13 in which $R_A$ is isoindol-5-yl, tetrahydroisoquinolin-5-yl, tetrahydroisoquinolin-6-yl, tetrahydroisoquinolin-7-yl, or tetrahydroisoquinolin-8-yl, each of which is substituted with 0 to 3 substituents independently chosen from $C_1$-$C_3$alkyl.

19. A compound or salt of claim 10 in which $R_A$ is dihydroindolyl, dihydroisoindolyl, tetrahydroisoquionolinyl, or tetrahydroquinolinyl, where $R_A$ is substituted with 0 to 2 substituents independently chosen from halogen, hydroxy, amino, $C_1$-$C_2$alkyl, and $C_1$-$C_2$alkoxy.

* * * * *